US008481029B2

(12) United States Patent
Glennie et al.

(10) Patent No.: US 8,481,029 B2
(45) Date of Patent: Jul. 9, 2013

(54) HUMAN IMMUNE THERAPIES USING A CD27 AGONIST ALONE OR IN COMBINATION WITH OTHER IMMUNE MODULATORS

(75) Inventors: Martin John Glennie, Southampton (GB); Alison Louise Tutt, Chilworth (GB); Aymen Al-Shamkhani, Otterbourne (GB)

(73) Assignee: University of Southampton, Highfield (GB)

( * ) Notice: Subject to any disclaimer, the term of this patent is extended or adjusted under 35 U.S.C. 154(b) by 0 days.

(21) Appl. No.: 12/446,322

(22) PCT Filed: Oct. 18, 2007

(86) PCT No.: PCT/US2007/022193
§ 371 (c)(1),
(2), (4) Date: Oct. 25, 2010

(87) PCT Pub. No.: WO2008/051424
PCT Pub. Date: May 2, 2008

(65) Prior Publication Data
US 2011/0033449 A1 Feb. 10, 2011

(30) Foreign Application Priority Data
Oct. 20, 2006 (GB) .................................. 0620894.6

(51) Int. Cl.
*A61K 39/395* (2006.01)
(52) U.S. Cl.
USPC ....................................................... 424/130.1
(58) Field of Classification Search
None
See application file for complete search history.

(56) References Cited

U.S. PATENT DOCUMENTS

| | | | | |
|---|---|---|---|---|
| 6,010,853 A * | 1/2000 | Kanteti et al. | ............... | 435/6.16 |
| 6,406,867 B1 * | 6/2002 | Yu et al. | ........................... | 435/7.2 |
| 2003/0035790 A1 * | 2/2003 | Chen et al. | ................... | 424/85.2 |
| 2003/0133936 A1 * | 7/2003 | Byrne et al. | ............... | 424/146.1 |
| 2006/0045883 A1 * | 3/2006 | Molldrem et al. | ......... | 424/185.1 |
| 2007/0148163 A1 | 6/2007 | Takahashi et al. | | |

FOREIGN PATENT DOCUMENTS
WO 2005/063981 A1 7/2005

OTHER PUBLICATIONS

Wischhusen et al., Cancer Research, 2002, 62: 2592-2599.*
Courdec et al., Cancer Gene Therapy, 1998, 5: 163-175.*
Rowley et al., J. Immunol., 2004, 172: 6039-6046.*
Takeda K. et al., CD27-Mediated Activation of Murine NK Cells; Journal of Immunology, American Association of Immunologists, vol. 164, No. 4, Feb. 15, 2000, pp. 1741-1745.
Hirano T. et al., CD27 synergizes with CD40 to induce IgM, IgG, and IgA antibody responses of peripheral blood B cells in the presence of IL-2 and IL-1; Immunology Letters, Oct. 31, 2003, vol. 89, No. 2-3, pp. 251-257.
Gravestein L.A. et al., Novel mAbs reveal potent co-stimulatory activity of murine CD27; International Immunology, Oxford University Press, GB, vol. 7, No. 4, Jan. 1, 1995, pp. 551-557.
Sugita K. et al., The 1A4 Molecule (CD27) is Involved in T Cell Activation; Journal of Immunology, Sep. 1, 1991, vol. 147, No. 5, pp. 1477-1483.
Van Lier R.A.W. et al., Tissue Distribution and Biochemical and Functional Properties of Tp55 (CD27), A Novel T Cell Differentiation Antigen; Journal of Immunology, vol. 139, No. 5, Sep. 1, 1987, pp. 1589-1596.
Florido M. et al., Contribution of CD30/CD153 but not of CD27/CD70, CD134/OX40L, or CD137/4-1BBL to the optimal induction of protective immunity to *Mycobacterium avium*, Journal of Leukocyte Biology, Nov. 2004, vol. 76, pp. 1039-1046.
Kobata T. et al., CD27-CD70 interactions regulate B-cell activation by T cells, Proceedings of the National Academy of Sciences, USA, Nov. 21, 1995, vol. 92, No. 24, pp. 11249-11253.
French R. et al., Eradication of lymphoma by CD8 T cells following anti-CD40 monoclonal antibody therapy is critically dependent on CD27 costimulation, Blood, Jun. 1, 2007, vol. 109, No. 11, pp. 4810-4815.
Supplementary European Search Report (EP App No. 07 85 2826) dated Nov. 8, 2010 (6 pages).
Lens, et al. "Control of lymphocyte function through CD27-CD70 interactions" Immunology, vol. 10, 1998, pp. 491-499.
Sakanishi T et al., Anti-tumor effects of depleting and non-depleting anti-CD27 monoclonal antibodies in immune-competent mice. Biochem Biophys Res Commun., Mar. 19, 2010 (Abstract).
Gravestein L et al., CD27 Cooperates with the Pre-T Cell Receptor in the Regulation of Murine T Cell Development. J. Exp. Med. Aug. 1, 1996, vol. 184, 675-685.

* cited by examiner

*Primary Examiner* — Ilia Ouspenski
(74) *Attorney, Agent, or Firm* — Hunton & Williams LLP

(57) ABSTRACT

Methods of inducing T cell proliferation and expansion in vivo for treating conditions wherein antigen-specific T cell immune response are therapeutically desirable such as cancer, infection, inflammation, allergy and autoimmunity and for enhancing the efficacy of vaccines are provided. These methods comprise the administration of at least one CD27 agonist, preferably an agonistic CD27 antibody, alone or in association with another moiety such as immune stimulant or immune modulator such as an anti-CD40, OX-40, 4-IBB, or CTLA-4 antibody or an agent that depletes regulatory cells, or a cytokine. These mono and combination therapies may also optionally include the administration of a desired antigen such as a tumor antigen, an allergen, an autoantigen, or an antigen specific to an infectious agent or pathogen against which a T cell response (often CD8+) is desirably elicited.

18 Claims, 10 Drawing Sheets

A
HUMAN IMMUNE THERAPIES USING A CD27 AGONIST ALONE OR IN COMBINATION WITH OTHER IMMUNE MODULATORS

FIELD OF THE INVENTION

The invention generally relates to the use of a CD27 agonist, preferably a CD27 agonistic antibody, as an adjuvant for promoting T-cell immunity in a subject in need thereof, e.g., a subject with cancer, infection, autoimmune disease, allergy or inflammatory disorder or a subject being administered a vaccine. Most preferably the CD27 agonist will be an intact human, humanized, or chimeric antibody or a fragment thereof or may comprise a single chain antibody such as an scFv that specifically binds human CD27. Alternatively, the agonist may comprise an engineered antibody which has been modified to enhance or diminish its interactions with host effector systems or to reduce adverse side effects. In some preferred embodiments the binding of these agonistic anti-CD70 antibodies to immune cells will not be blocked by CD70 or related ligands.

Additionally, the invention provides novel adjuvant combinations, preferably synergistic combinations, for eliciting an enhanced T cell immune response in a subject in need thereof comprising (i) at least one CD27 agonist and (ii) another immunostimulant or immunomodulator, e.g. a CD40 antibody, CD28 antibody, OX40 antibody, 4-1BB antibody, anti-CTLA-4, TLR (toll like receptor) agonist or a moiety that depletes regulatory T cells, or a cytokine such as an interleukin e.g., IL-2 or an interferon (beta, beta, gamma, et al.). Similarly, these adjuvant combinations are useful in treating conditions wherein enhanced T cell immunity is therapeutically desired such as cancer, infectious diseases, allergy, autoimmunity, inflammatory disorders and for enhancing the efficacy of vaccines.

The subject monotherapies involving the administration of a CD27 agonist. preferably an agonistic CD27 antibody the binding of which to immune cells is preferably is not blocked by CD70 and combination therapies involving the administration of a CD27 agonist and another moiety such as another immune modulator or therapeutic agent are useful in enhancing CTL immunity and T cell proliferation and survival in vivo. As discussed in greater detail infra, this invention is based at least in part on the inventors' surprising observation that CD27: CD70 interactions are required for the agonistic activity of CD40 antibodies (anti-CD70 mAb completely blocks the activity of agonistic CD40 showing that CD27: CD70 interactions are required 'downstream' of CD40 triggering). This observation suggested the therapeutic potential of CD27 agonistic antibodies as therapeutic adjuvants and for activating and inducing the expansion of antigen-specific T cells, particularly CD8+ T cells i.e., effector and memory CD8+ effector cells. While Applicants do not want to be bound by their hypothesis, they theorize that the agonistic property of the subject anti-CD27 antibodies on T cells may be attributable, at least in part, to the fact that the binding of such antibodies may not be blocked by CD70. However, the invention is not limited thereto and embraces the use of any anti-CD27 agonistic antibody or conjugate or fragment thereof that has an agonistic effect on T cell immunity. As described in detail infra, the present mono and combination therapies are especially useful in treating humans or other mammals with lymphomas and other cancers or infectious conditions wherein enhanced antigen-specific CTL immune responses are therapeutically desirable.

As noted the CD27 agonist may be administered alone or in conjunction with other therapeutic moieties such as other immune adjuvants or immunostimulators or immune modulators, with or without a suitable antigen, such as a cancer peptide. For example, in one embodiment the CD27 agonist may be administered in association with a CD40 agonistic antibody. In this embodiment of the invention the CD40 agonist may comprise a chimeric agonistic anti-human CD40 antibody referred to herein as LOB 7/4 or a humanized variant thereof. This chimeric antibody has been demonstrated by the inventors to elicit potent anti-tumor effects on a range of CD40 expressing tumors and to potentiate cellular immunity. Based on these results the use of this chimeric antibody and variants thereof, e.g., human or humanized versions thereof as an immune adjuvant or therapeutic for treating various chronic diseases including cancers (CD40 positive and negative), especially solid tumors as well as its use as an immune adjuvant for treating infectious diseases, autoimmune diseases, allergic and inflammatory diseases are taught in an earlier patent application by some of the inventors herein.

In preferred embodiments of the invention the subject CD27 agonist is used to treat cancer, infectious diseases, autoimmune disorders, allergic disorders, or inflammatory disorders alone or with an antigen or is administered in conjunction with a vaccine or other therapeutic agents or immunotherapeutic, e.g., an antibody to CD40, OX40, CD28, CTLA-4, or 4-1BB; a TLR agonist; a moiety that depletes regulatory T cells; a cytokine; an anti-angiogenesis agent; or a chemotherapeutic. Throughout this application when combination therapies are mentioned, it should be understood that the respective moieties such as agonistic antibodies may be administered separately or in combination, e.g. in the same or different compositions, and administration of the respective moieties may be effected in any order. Also, these combination and monotherapies are intended to embrace the administration of additional moieties useful in treating the particular disease or condition.

BACKGROUND OF THE INVENTION

It is now widely recognized that the generation of protective immunity depends not only on exposure to antigen, but also the context in which the antigen is encountered. Numerous examples exist in which introduction of a novel antigen into a host in a non-inflammatory context generates immunological tolerance rather than long-term immunity whereas exposure to antigen in the presence of an inflammatory agent (adjuvant) induces immunity. (Mondino et al., Proc. Natl. Acad. Sci., USA 93:2245 (1996); Pulendran et al., J. Exp. Med. 188:2075 (1998); Jenkins et al., Immunity 1:443 (1994); and Kearney et al., Immunity 1:327 (1994)). Since it can mean the difference between tolerance and immunity, much effort has gone into discovering the "adjuvants" present within infectious agents that stimulate the molecular pathways involved in creating the appropriate immunogenic context of antigen presentation.

CD27 is a member of the tumor necrosis factor receptor (TNFR) super family which also includes TNFR type I and II (CD120a and b), nerve growth factor receptor (NGFR), CD30, Fas/Apo-1 (CD95), CD40, 4-1BB and OX40. These proteins are known to play key roles in cell growth, survival, and differentiation as well as apoptosis or programmed cell death. Homology among these family members is restricted to the extracellular region and is characterized by the presence of a cysteine knot motif which occurs three times in CD27 (McDonald et al., Cell 73:4121-424 (1993)).

CD27 is a glycosylated, type I transmembrane protein of about 55 kilodaltons and exists as homodimers with a disulfide bridge linking the two monomers. The disulfide bridge is in the extracellular domain close to the membrane (Camerini et al., J. Immunol. 147:3165-69 (1991)). The ligand for CD27, CD70, belongs to the TNF family of ligands. CD70 is a type II transmembrane protein with an apparent molecular weight of 50 kd (Goodwin et al., Cell 73:447-456 (1993)). Based on homology to TNF alpha and beta, CD70 was predicted to have a trimeric structure made up of three identical subunits which interact with three CD27 homodimers (Peitsch et al., Mol. Immunol. 152:1756-1761 (1994)). TNF alpha which also is a type II transmembrane protein, is released from the cell by proteolytic cleavage, whereas TNF beta and NGF are secreted.

CD27 and its ligand CD70 are expressed on discrete populations of T and B cells. CD27 is expressed on resting T cells and CD70 on activated T and B cells and dendritic cells. Within T cell subsets, CD27 is stably expressed on CD45R+ cells even after activation, whereas on CD45RO+ cells it is weakly expressed and lost after activation. (Sugita et al., J. Immunol. 149:3208-3216 (1992); Hintzen et al., J. Immunol. 151:2426-2435 (1993)). On CD45RA+ cells, activation by various means results in the upregulation of CD27 expression (Hintzen et al., J. Immunol. 151:2426-2435 (1993)). CD27 is highly expressed on most of the B cell non-Hodgkin's lymphomas and B cell chronic lymphocytic leukemias. (Ranheim et al., Blood 85:3556-3565) The B cell lines Ramos and Raji, also express significant levels of CD27 and CD70.

Ligation of CD27 along with treatment of T cells with sub-optimal dose of PMA, PHA, anti-CD2 or anti-CD3 antibodies is also known to result in the proliferation of T cells, thus defining a co-stimulatory role for CD27. It has also been reported that CD27-mediated co-stimulatory effects can be specifically inhibited using an anti-CD27 antibody or recombinant soluble CD27 or anti-CD70 antibody and that ligation of CD27 via its ligand, CD70 can generate cytolytic T cells. (Goodwin et al., Cell 73:447-456 (1993)).

Another co-stimulatory molecule which is known to regulate adaptive immunity is CD40. CD40 is a member of the TNF receptor superfamily and is essential for a spectrum of cell-mediated immune responses and required for the development of T cell dependent humoral immunity (Aruffo et al., Cell 72:291 (1993); Farrington et al., Proc Natl Acad. Sci., USA 91:1099 (1994); Renshaw et al., J Exp Med 180:1889 (1994)). In its natural role, CD40-ligand expressed on CD4+ T cells interacts with CD40 expressed on DCs or B cells, promoting increased activation of the APC and, concomitantly, further activation of the T cell (Liu et al Semin Immunol 9:235 (1994); Bishop et al., Cytokine Growth Factor Rev 14:297 (2003)). For DCs, CD40 ligation classically leads to a response similar to stimulation through TLRs such as activation marker upregulation and inflammatory cytokine production (Quezada et al. Annu Rev Immunol 22:307 (2004); O'Sullivan B and Thomas R Crit. Rev Immunol 22:83 (2003)) Its importance in CD8 responses was demonstrated by studies showing that stimulation of APCs through CD40 rescued CD4-dependent CD8+ T cell responses in the absence of CD4 cells (Lefrancois et al., J. Immunol. 164:725 (2000); Bennett et al., Nature 393:478 (1998); Ridge et al., Nature 393:474 (1998); Schoenberger et al., Nature 393:474 (1998). This finding sparked much speculation that CD40 agonists alone could potentially rescue failing CD8+ T cell responses in some disease settings (French et al., Nature Medicine 1999).

Other studies, however, have demonstrated that CD40 stimulation alone insufficiently promotes long-term immunity. In some model systems, anti-CD40 treatment alone insufficiently promoted long-term immunity, i.e., yields ineffective inflammatory cytokine production. as well as the deletion of antigen-specific T cells (Mauri et al. Nat Med 6:673 (2001); Kedl et al. Proc Natl Acad. Sci., USA 98:10811 (2001)) and termination of B cell responses (Erickson et al., J Clin Invest 109:613 (2002)). Also, soluble trimerized CD40 ligand has been used in the clinic as an agonist for the CD40 pathway and what little has been reported is consistent with the conclusion that stimulation of CD40 alone fails to reconstitute all necessary signals for long term CD8+ T cell immunity (Vonderheide et al., J Clin Oncol 19:3280 (2001)).

Both agonistic and antagonistic antibodies specific to CD40 have been suggested to have potential as human therapeutics. Antagonistic anti-CD40 antibodies include those that (1) block CD40/CD40L interaction by at least 90% and have purported antineoplastic properties (Armitage et al., U.S. Pat. No. 5,674,492; Fanslow et al., 1995, Leukocyte Typing V Schlossman et al., eds., 1:555-556); (2) those that antagonize signaling through CD40 (deBoer et al., U.S. Pat. No. 5,677, 165) and (3) those that deliver a stimulatory signal through CD40 but do not increase the interaction between CD40 and CD40L, e.g., G28-5, (Ledbetter et al., U.S. Pat. No. 5,182, 368; PCT WO 96/18413).

Agonistic anti-CD40 antibodies have been reported by several groups. For example, one mAb, CD40.4 (5C3) (PharMingen, San Diego, Calif.) has been reported to increase the interaction between CD40 and CD40L by approximately 30-40% (Schlossman et al., eds., Leukocyte Typing, 1995, 1:547-556). Additionally, Seattle Genetics in U.S. Pat. No. 6,843,989 allege to provide methods of treating cancer in humans using anti-human CD40 antibodies. These antibodies are alleged to deliver a stimulatory signal, to enhance the interaction between CD40 and CD40L by at least 45% and to enhance CD40L-mediated stimulation and to possess in vivo neoplastic activity. The exemplified antibody disclosed in the Seattle Genetics patent was derived from S2C6, an agonistic anti-human CD40 antibody previously shown to deliver strong growth-promoting signals to B lymphocytes (Paulie et al., 1989, J. Immunol. 142:590-595).

However, notwithstanding these prior reports, improved methods and human therapies using adjuvants that promote Th1 immunity and which enhance the activation and expansion of antigen specific CD8+ T cells, i.e. CD8+ effector and memory cells are needed. Particularly, improved methods of treating human cancer and other diseases using therapeutic adjuvants which are safe and effective, i.e., which do not elicit undesired side effects but which elicit substantial therapeutic effects, e.g., anti-tumor effects are needed. The present invention satisfies this need and provides other advantages as well.

SUMMARY OF THE INVENTION

This invention provides novel methods of human treatment using a CD27 agonist such as an agonistic CD27 antibody alone or in conjunction with another therapeutic agent, e.g. another immunostimulant or immunomodulatory agent such as an agonistic CD40 antibody, soluble CD40L, a 4-1BB:4-1BBL agonist, an OX40 agonist, TLR agonist, a moiety that depletes regulatory T cells, or a cytokine such as an interleukin or an interferon. As noted above in preferred embodiments the binding of these CD27 agonistic antibodies to immune cells will not be blocked by CD70 as this may have a beneficial effect on the agonistic activity of these antibodies on T cells. These combinations would normally be employed together with a vaccine in the form or protein, peptides, immunogenic cells, or DNA. The results infra show that blocking the co-stimulation of CD27 has a profound effect on anti-tumor immunity elicited by an agonistic anti-CD40 antibody much more than blocking 4-1BB co-stimulation, and that this is apparently the result of a severe impairment in CD8+ T cell expansion during CD27-CD70 blockade. These results suggest that CD27 agonists, e.g., agonist anti-CD27 antibodies may be used as therapeutic adjuvants for promoting CD8+ T cell expansion and in treating conditions wherein this is therapeutically desirable such as cancer, infectious disorders, autoimmunity, allergic disorders, and inflammatory disorders. Also, it suggested that a CD27 agonist, e.g., a CD27 agonistic antibody may be administered in association with an antigen or vaccine in order to promote antigen-specific CD8+ T cell immunity. In an especially preferred embodiment the CD27 agonist will be used to treat a cancer such as a lymphoma or other cancers identified infra.

While the mechanism by which anti-CD40 monoclonal antibodies generate immune responses against tumors in humans and rodents is not fully understood, it appears to operate through the stimulation of dendritic cells to a level that boosts CTL responses and circumvents the need for CD4 helper cells. It is shown herein that agonistic CD40 monoclonal antibody promotes strong expression of 4-1BB on the expanding CD8 cells, together with a modest loss of CD27 as effector CTL are generated. Interestingly, while CD40 mAb treatment caused a profound activation of dendritic cells in tumor-bearing mice, the expression of 4-1BBL and CD70, the respective ligands for 4-1BB and CD27, was relatively weak and transient. Despite this lack of expression their involvement was established by showing that mAb (AT113-2:anti-4-1BBL, and TAN1-6:anti-CD70), which blocked the interaction CD70 block in the therapeutic efficacy of CD40 mAb treatment. Likewise they had no influence on the cytotoxic activity of tumor-specific CTL cells either in vitro or in vivo. Based thereon, the present inventors concluded that 4-1BB: 4-1BBL and particularly CD27: CD70 interactions are pivotal in explaining the activity of CD40 agonistic antibodies and that these antibodies act by triggering CD8 T cell proliferation and survival. Moreover, the inventors show for the first time herein that an agonistic anti-CD27 antibody is highly effective by itself in protecting lymphoma-bearing mice (A31 and BCL1) indicating that CTL can be generated at a later stage than DC and that agonistic CD27 antibodies may be used to treat cancer and other diseases wherein enhanced cellular immunity is necessary. Importantly, this anti-CD27 mAb did not protect immunocompromised SCID mice from these same tumors, underlining the need for a functional immune system (CD8 T cells) to provide this protection.

Therefore, this invention provides novel mono and combination therapies for promoting T cell immunity in a subject in need thereof, e.g., a subject with lymphoma comprising the administration of at least one CD27 agonist and optionally another moiety such as a CD40 agonist. As noted above, if a CD40 agonist is utilized in association with the subject CD27 agonistic antibody, the CD40 agonist will preferably comprise an anti-human CD40 antibody e.g., a chimeric antibody referred to herein as LOB 7/4 or a derivative thereof, e.g., humanized antibodies or fragments thereof containing the variable heavy and light sequences or CDRs derived from the LOB 7/4 antibody. The present inventors have found that this chimeric antibody possesses advantageous properties when used as a therapeutic, e.g. for treatment of cancer, especially CD40 expressing lymphomas and solid tumors.

DETAILED DESCRIPTION OF THE INVENTION

Figure 1A:
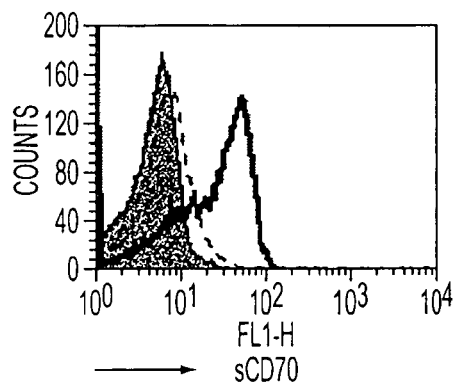
FIG. 1 contains the results of an experiment which shows that TAN1-6 (anti-CD70 antibody) and AT113-2 (anti-4-1BBL) block the 4-1BB and CD70/CD27 interactions respectively in vitro and during in vivo responses.

Interactions between members of the TNFR superfamily and their TNF family ligands play a critical role in providing co-stimulation at several stages during the development of an effective, antigen-specific CD8 T-cell response to pathogens and tumors. Early in the response, the ligation of CD40 on dendritic cells (DC) by its ligand, CD154 (CD40L), on activated Th cells, induces the activation, or licensing, of DCs and potentiates their ability to present antigen to naïve CD8 T cells (Bennett, Carbone et al. 1998; Ridge, Di Rosa et al. 1998; Toes, Schoenberger et al. 1998). Anti-CD40 mAb or soluble CD40 ligand (CD40L), which can substitute for Th cells for DC licensing, have been shown to have therapeutic potential in a number of settings requiring T cell responses, including vaccination, and treatment of tumors, (French, Chan et al. 1999; Tutt, O'Brien et al. 2002; van Mierlo, den Boer et al. 2002; Murray, Lu et al. 2003) viruses and infections (Rolph and Kaufman 2001; Murray, Lu et al. 2003). The CD40-induced activation of DC is characterized by an increase in their expression of adhesion and co-stimulatory molecules, including ICAM-1, B7.1, B7.2, CD70 and 4-1BB ligand (4-1BBL) (Cella, Scheidegger et al. 1996; Diehl, van Mierlo et al. 2002; Tesselaar, Xiao et al. 2003)). While initial antigen-specific CTL activation/priming is dependent on the CD28:B7 engagement (Lenschow, Walunas et al. 1996; Carreno and Collins 2002)), subsequent expansion and survival of effector cells is controlled by a plethora of additional co-stimulatory interactions. The precise role of each of these pathways in maintaining memory responses is currently an area of active investigation. Two receptors which appear critical in maintaining CTL responses are the TNFR-family members 4-1BB (CD137) (DeBenedette, Shahinian et al. 1997; Futagawa, Akiba et al. 2002) and CD27 (Tesselaar, Xiao et al. 2003), which interaction with their respective ligands, 4-1BBL and CD70 expressed mainly on DC. For example, it is known that, while anti-CD40 mAb driven CTL responses are helper independent, they remain dependent on both CD28:B7 and CD27:CD70 interactions ((Prilliman, Lemmens et al. 2002; Tutt, O'Brien et al. 2002; Taraban, Rowley et al. 2004). Less information is currently known of the importance of 4-1BB during anti-CD40 mAb driven CTL responses, but it is clear that T-helper cell-dependent priming of CTL is at least partially dependent on 4-1BB and is markedly compromised by 4-1BB blockade (Diehl, van Mierlo et al. 2002).

The present inventors have previously demonstrated that anti-CD40 mAb stimulates a helper-independent CTL response against a number of syngeneic lymphomas, that successfully eradicates existing tumors, and leaves the mice resistant to rechallenge (French, Chan et al. 1999; Tutt, O'Brien et al. 2002). Early clinical trials with anti-CD40 mAb shows clinical success and patient benefit.

By contrast this invention relates to the role of CD27 as a therapeutic immune adjuvant and for promoting CD8+ T cell immunity, e.g., in lymphoma subjects. In an Ova model system, the inventors have recently shown that costimulation via CD27 is essential for CD40 mAb-mediated priming of ovalbumin-specific CTLs. Although priming of endogenous ovalbumin-specific T cells was not seen when CD70-CD27 interaction was abrogated, the priming of ovalbumin-specific TCR transgenic T cells (OT-I) was detected, albeit at markedly reduced level. Furthermore, while OT-I T cells primed in the absence of CD27 signaling were able to differentiate into cytotoxic T cells, their ability to mount a secondary response was defective. In light of these findings we wished to address the role of CD27 costimulation in CD40 mAb-mediated immunotherapy of lymphoma and to compare that with the role of its close relative 4-1BB. The results of these studies which are provided in the examples infra show that blocking co-stimulation via CD27 has a more effect on the anti-tumor response elicited by an agonistic antibody and this effect is much more pronounced than blocking 4-IBB co-stimulation. The inventors further believe that this is due to a severe impairment in CD8+ T cell expansion during CD27-CD70 blockade.

Based thereon, the present invention provides novel methods of human therapy by administering an immunologically promoting (adjuvant) or therapeutically effective amount of (i) at least one CD27 agonist and (ii) optionally another therapeutic moiety which may comprise another immunomodulator or immunostimulant such as a CD40 agonist, an OX-40 agonist, a 4-1BB agonist, anti-CTLA-4, a moiety that depletes regulatory T cells (Treg), or a cytokine such as an interferon or interleukin or may comprise a drug or chemotherapeutic agent. The CD27 agonist alone or in combination results in the potentiation of the increase in CD8+ T cell proliferation and CTL immune responses, e.g., those elicited by an CD40 agonist such as an agonistic CD40 antibody.

The present invention further provides for the first time agonistic anti-CD27 antibodies useful for promoting T cell immunity. In a preferred embodiment the binding of these agonistic antibodies will not be affected (inhibited) by CD70. While this is not essential to the present invention, it is believed that agonistic antibodies that do not compete with CD70 may possess advantageous properties when used as immune adjuvants, e.g., in the treatment of cancers such as lymphomas.

The CD27 agonist will preferably comprise an agonistic anti-CD27 antibody. This antibody which may or may not compete with CD70 will preferably comprise a human, humanized, chimeric agonistic anti-human CD27 antibody that preferably comprises a human constant domain which may be an IgG1, IgG2, IgG3 IgG4, IgM, IgD, IgE, IgA1 or IgA2 human constant domain. These constant domains may be modified if desired in order to enhance or modify effector function. Also, the antibody may be mutated to remove or alter glycosylation. Similarly, if another agonistic antibody is used along with the CD27 agonistic antibody they similarly will preferably be human, humanized or chimeric antibodies preferably containing a human constant domain and may be mutated as described above with respect to the CD27 agonistic antibody. Also, single chain antibodies and antibody fragments are within the scope of the invention such as Fabs, scFvs, minibodies and the like.

In an exemplary embodiment if a CD40 agonist is co-administered with the CD27 agonist the CD40 agonist will comprise a chimeric anti-human CD40 antibody referred to herein as LOB 7/4, or a variant thereof, or a fragment thereof, especially humanized versions thereof, and/or antibodies antibody fragments which possess the same epitopic specificity as LOB 7/4 or which compete with LOB 7/4 for binding to human CD40.

In an exemplary embodiment the present invention provides novel methods of treating human cancer, such as solid tumors and lymphomas by administering a therapeutically effective amount of a CD27 agonist such as an agonistic anti-CD27 antibody. Optionally, this agonist may be administered in association with another agonist or cytokine, e.g., one which elicits a synergistic effect therewith such as a CD40 agonist, a 4-1BB:4-1BBL agonist such as a 4-1BBL agonistic antibody, a 4-1BB agonist such as an agonistic 4-1BB antibody, anti-CTLA-4 or an interleukin such as IL-2 or an interferon such as an alpha, beta, or gamma interferon or a moiety that results in Treg depletion. These immune combination may be administered together or in combination. These agonists or agonist/cytokine combinations may be in the same composition or different compositions. Preferably they are administered synchronous or close to synchronous to each other. Typically, these therapeutic moieties are administered within 24 hours of each other, more typically within 8 hours, and still more typically within 1-4 hours of each other.

Cancers treatable with the subject CD27 agonist, i.e., CD27 agonistic antibody include by way of example leukemia, acute lymphocytic leukemia, acute myelocytic leukemia, myeloblastic promyelocytic myelomonocytic monocytic erythroleukemia, chronic leukemia, chronic myelocytic (granulocytic) leukemia, chronic lymphocytic leukemia, Polycythemia vera Lymphoma, Hodgkin's disease, non-Hodgkin's disease, multiple myeloma, Waldenstrom's macroglobulinemia, heavy chain disease, solid tumors, sarcomas, and carcinomas, fibrosarcoma, myxosarcoma, liposarcoma, chrondrosarcoma, osteogenic sarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon sarcoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular tumor, lung carcinoma, small cell lung carcinoma, non small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, retinoblastoma, nasopharyngeal carcinoma, and esophageal carcinoma. In preferred embodiments the subject antibody is used to treat CD40 expressing solid tumors such as CD40 expressing melanoma, non-small lung carcinoma, invasive duct breast carcinoma, diffuse large B cell lymphoma, and other solid tumors which express CD40.

Still further the invention provides novel methods of potentiating cellular immunity in a human subject in need of such treatment by administering an amount of the subject adjuvant agonist combination to a patient in need thereof alone or in combination with another active agent such as a cytokine and optionally an antigen.

Additionally, the present invention is directed to treating human inflammatory diseases and deficiencies using the subject adjuvant combination alone or in conjunction with other immune- and non-immune-based therapeutics. Such conditions include by way of example systemic lupus erythematosus (SLE), scleroderma (e.g., CRST syndrome), inflammatory myositis, Sjogren's syndrome (SS), mixed connective tissue disease (e.g., MCTD, Sharp's syndrome), rheumatoid arthritis, multiple sclerosis, inflammatory bowel disease (e.g., ulcerative colitis, Crohn's disease) acute respiratory distress syndrome, pulmonary inflamation, osteoporosis, delayed type sensitivity, asthma, primary biliary cirrhosis (PBC), and idiopathic thromboctytopenic purpura (ITP).

The subject methods which preferably administer an agonistic anti-human CD27 antibody and optionally another immune stimulant or immune modulator such as an agonistic CD40, OX-40, 4-1BB, or CTLA-4 antibody, moiety that depletes regulatory T cells or a cytokine will be administered to a host in need of such treatment in order to elicit an enhanced antigen specific antitumor or cellular immune response. In preferred embodiments these antibodies will be administered to a subject having or at risk of developing a cancer, an infection, particularly a chronic infectious diseases e.g., involving a virus, bacteria or parasite; or an autoimmune, inflammatory or allergic condition. For example the subject antibody or combination can be used to elicit antigen specific cellular immune responses against HIV. HIV is a well recognized example of a disease wherein protective immunity almost certainly will require the generation of potent and long-lived cellular immune responses against the virus.

As noted, this invention provides agonistic antibody therapies and combination therapies which can be used in the treatment of chronic infectious diseases involving viruses, bacteria, fungi or parasites as well as proliferative diseases such as cancer, autoimmune diseases, allergic disorders, and inflammatory diseases where effective treatment requires the elicitation of a potent cellular antigen specific immune response.

The subject CD27 agonist may optionally be administered in combination with other immune adjuvants such as lymphokines and cytokines. Examples thereof include interferons such as alpha, beta, and gamma interferon, interleukins such as IL-2, 11-4, IL-6, IL-13 et al., colony stimulating factors, TNFs, and the like.

Additionally, the subject anti-human CD40 antibodies may be administered in combination with other antitumor agents such as chemotherapeutics and cytotoxins commonly used for treating cancer, agents that inhibit angiogenesis, and the like. These additional therapeutic agents may be administered separately or in combination with the subject agonistic anti-CD27 antibody. Also, in some embodiments an effector moiety such as a chemotherapeutic may be directly or indirectly attached to the subject anti-human CD27 or other optionally included agonistic antibody such as anti-human CD40, anti-OX-40, anti-4-1BB, anti-CTLA-4 etc. e.g., by the use of a linker.

Further, in some embodiments the subject anti-human CD27 antibody or therapeutic combination containing an agonistic CD27 antibody may be administered in combination with a desired antigen or attached to an antigen.

Exemplary antigens include but are not limited to bacterial, viral, parasitic, allergens, autoantigens and tumor associated antigens. If a DNA based vaccine is used the antigen will be encoded by a sequence the administered DNA construct. Alternatively, if the antigen is administered as a conjugate the antigen will be a protein comprised in the administered conjugate. Still further, the antigen is administered separately from the CD27 antibody and the antigen can take any form. Particularly, the antigen can include protein antigens, peptides, whole inactivated organisms, and the like.

Specific examples of antigens that can be used in the invention include antigens from hepatits A, B, C or D, influenza virus, *Listeria, Clostridium botulinum*, tuberculosis, tularemia, Variola major (smallpox), viral hemorrhagic fevers, *Yersinia pestis* (plague), HIV, herpes, pappilloma virus, and other antigens associated with infectious agents. Other antigens include antigens associated with a tumor cell, antigens associated with autoimmune conditions, allergy and asthma. Administration of such an antigen in conjunction with the subject agonistic anti-CD27 antibody can be used in a therapeutic or prophylactic vaccine for conferring immunity against such disease conditions.

In some embodiments the methods and compositions can be used to treat an individual at risk of having an infection or has an infection by including an antigen from the infectious agent. An infection refers to a disease or condition attributable to the presence in the host of a foreign organism or an agent which reproduce within the host. A subject at risk of having an infection is a subject that is predisposed to develop an infection. Such an individual can include for example a subject with a known or suspected exposure to an infectious organism or agent. A subject at risk of having an infection can also include a subject with a condition associated with impaired ability to mount an immune response to an infectious agent or organism, for example a subject with a congenital or acquired immunodeficiency, an infant, an elderly person, a subject undergoing radiation or chemotherapy, a subject with a burn injury, a subject with a traumatic injury, a subject undergoing surgery, or other invasive medical or dental procedure, or other immunocompromised individual.

Infections which may be treated or prevented using the subject agonistic antibody combinations potentially in combination with other immune potentiators include bacterial, viral, fungal, and parasitic infections. Other less common types of infections also include are rickettsiae, mycoplasms, and agents causing scrapie, bovine spongiform encephalopathy (BSE), and prion diseases (for example kuru and Creutzfeldt-Jacob disease). Examples of bacteria, viruses, fungi, and parasites that infect humans are well known. An infection may be acute, subacute, chronic or latent and it may be localized or systemic. Furthermore, the infection can be predominantly intracellular or extracellular during at least one phase of the infectious organism's agent's life cycle in the host.

Bacterial infections against which the subject antibodies may be used to potentiate a cellular immune response include both Gram negative and Gram positive bacteria. Examples of Gram positive bacteria include but are not limited to *Pasteurella* species, *Staphylococci* species, and *Streptococci* species. Examples of Gram negative bacteria include but are not limited to *Escherichia coli*, *Pseudomonas* species, and *Salmonella* species. Specific examples of infectious bacteria include but are not limited to *Heliobacter pyloris*, *Borrelia burgdorferi*, *Legionella pneumophilia*, *Mycobacteria* spp. (for example *M. tuberculosis*, *M. avium*, *M. intracellilare*, *M. kansaii*, *M. gordonae*), *Staphylococcus aureus*, *Neisseria gonorrhoeae*, *Neisseria meningitidis*, *Listeria monocytogeners*, *Streptococcus pyogenes*, (group A *Streptococcus*), *Streptococcus agalactiae* (Group B *Streptococcus*), *Streptococcus* (viridans group), *Streptococcus faecalis*, *streptococcus bovis*, *Streptococcus* (aenorobic spp.), *Streptococcus pneumoniae*, pathogenic *Campylobacter* spp., *Enterococcus* spp., *Haemophilus influenzae*, *Bacillus anthracis*, *Corynebacterium diptheriae*, *Corynebacterium* spp., *Erysipelothrix rhusiopathie*, *Clostridium perfringens*, *Clostridium tetani*, *Enterobacter aerogenes*, *Klebsiella pneumoniae*, *Pasteurella multocida*, *Bacteroides* spp., *Fusobacterium nucleatum*, *Streptobacillus moniliformis*, *Treponema pallidum*, *Treponema pertenue*, *Leptospira*, *Rickettsia*, and *Actinomyces israelii*.

Examples of viruses that cause infections in humans include but are not limited to Retroviridae (for example human deficiency viruses, such as HIV-1 (also referred to as HTLV-III), HIV-II, LAC or IDLY-III/LAV or HIV-III and other isolates such as HIV-LP, Picornaviridae (for example poliovirus, hepatitis A, enteroviruses, human Coxsackie viruses, rhinoviruses, echoviruses), Calciviridae (for example strains that cause gastroenteritis), Togaviridae (for example equine encephalitis viruses, rubella viruses), Flaviviridae (for example dengue viruses, encephalitis viruses, yellow fever viruses) Coronaviridae (for example coronaviruses), Rhabdoviridae (for example vesicular stomata viruses, rabies viruses), Filoviridae (for example Ebola viruses) Paramyxoviridae (for example parainfluenza viruses, mumps viruses, measles virus, respiratory syncytial virus), Orthomyxoviridae (for example influenza viruses), Bungaviridae (for example Hataan viruses, bunga viruses, phleoboviruses, and Nairo viruses), Arena viridae (hemorrhagic fever viruses), Reoviridae (for example reoviruses, orbiviruses, rotaviruses), Bimaviridae, Hepadnaviridae (hepatitis B virus), Parvoviridae (parvoviruses), Papovaviridae (papilloma viruses, polyoma viruses), Adenoviridae (adenoviruses), Herpeviridae (for example herpes simplex virus (HSV) I and II, varicella zoster virus, pox viruses) and Iridoviridae (for example African swine fever virus) and unclassified viruses (for example the etiologic agents of Spongiform encephalopathies, the agent of delta hepatitis, the agents of non-A, non-B hepatitis (class 1 enterally transmitted; class 2 parenterally transmitted such as Hepatitis C); Norwalk and related viruses and astroviruses).

Examples of fungi include *Aspergillus* spp., *Coccidoides immitis*, *Cryptococcus neoformans*, *Candida albicans* and other *Candida* spp., *Blastomyces dermatidis*, *Histoplasma capsulatum*, *Chlamydia trachomatis*, *Nocardia* spp., and *Pneumocytis carinii*.

Parasites include but are not limited to blood-borne and/or tissue parasites such as *Babesia microti*, *Babesi divergans*, *Entomoeba histolytica*, *Giardia lamblia*, *Leishmania tropica*, *Leishmania* spp., *Leishmania braziliensis*, *Leishmania donovdni*, *Plasmodium falciparum*, *Plasmodium malariae*, *Plasmodium ovale*, *Plasmodium vivax*, *Toxoplasma gondii*, *Trypanosoma gambiense* and *Trypanosoma rhodesiense* (African sleeping sickness), *Trypanosoma cruzi* (Chagus' disease) and *Toxoplasma gondii*, flat worms, and round worms.

As noted this invention preferably is preferably directed to the use of an agonistic anti-human CD27 antibody optionally in association with another moiety such as an agonistic anti-human CD40, OX-40, CTLA-4, 4-1BB antibody or a cytokine or agent that depletes regulatory T cells in treating proliferative diseases such as cancers. Cancer is a condition of uncontrolled growth of cells which interferes with the normal functioning of bodily organs and systems. A subject that has a cancer is a subject having objectively measurable cancer cells present in the subjects' body. A subject at risk of developing cancer is a subject predisposed to develop a cancer, for example based on family history, genetic predisposition, subject exposed to radiation or other cancer-causing agent. Cancers which migrate from their original location and seed vital organs can eventually lead to the death of the subject through the functional deterioration of the affected organ. Hematopoietic cancers, such as leukemia, are able to out-compete the normal hematopoietic compartments in a subject thereby leading to hematopoietic failure (in the form of anemia, thrombocytopenia and neutropenia), ultimately causing death.

The compositions of the invention comprising a CD27 agonist and optionally another moiety as mentioned above can be used to treat a variety of cancers or subjects at risk of developing cancer, e.g., by the inclusion of a tumor-associated-antigen (TAA). This is an antigen expressed in a tumor cell. Examples of such cancers include breast, prostate, colon, blood cancers such as leukemia, chronic lymphocytic leukemia, and the like. A tumor associated antigen can also be an antigen expressed predominantly by tumor cells but not exclusively.

Additional cancers include those already mentioned as well as basal cell carcinoma, biliary tract cancer, bladder cancer, bone cancer, brain and central nervous system (CNS) cancer, cervical cancer, choriocarcinoma, colorectal cancers, connective tissue cancer, cancer of the digestive system, endometrial cancer, esophageal cancer, eye cancer, head and neck cancer, gastric cancer, intraepithelial neoplasm, kidney cancer, larynx cancer, liver cancer, lung cancer (small cell, large cell), lymphoma including Hodgkin's lymphoma and non-Hodgkin's lymphoma; melanoma; neuroblastoma; oral cavity cancer (for example lip, tongue, mouth and pharynx); ovarian cancer; pancreatic cancer; retinoblastoma; rhabdomyosarcoma; rectal cancer; cancer of the respiratory system; sarcoma; skin cancer; stomach cancer; testicular cancer; thyroid cancer; uterine cancer; cancer of the urinary system; as well as other carcinomas and sarcomas.

The subject CD27 agonist, and compositions containing or combination therapies as defined previously can also be used to treat autoimmune diseases such as multiple sclerosis, rheumatoid arthritis, type 1 diabetes, psoriasis or other autoimmune disorders. Other autoimmune disease which potentially may be treated with the immune adjuvants of the invention include Crohn's disease and other inflammatory bowel diseases such as ulcerative colitis, systemic lupus eythematosus (SLE), autoimmune encephalomyelitis, myasthenia gravis (MG), Hashimoto's thyroiditis, Goodpasture's syndrome, pemphigus, Graves disease, autoimmune hemolytic anemia, autoimmune thrombocytopenic purpura, scleroderma with anti-collagen antibodies, mixed connective tissue disease, polypyositis, pernicious anemia, idiopathic Addison's disease, autoimmune associated infertility, glomerulonephritis) for example crescentic glomerulonephritis, proliferative glomerulonephritis), bullous pemphigoid, Sjogren's syndrome, psoriatic arthritis, insulin resistance, autoimmune diabetes mellitus (type 1 diabetes mellitus; insulin dependent diabetes mellitus), autoimmune hepatitis, autoimmune hemophilia, autoimmune lymphoproliferative syndrome (ALPS), autoimmune hepatitis, autoimmune hemophilia, autoimmune lymphoproliferative syndrome, autoimmune uveoretinitis, and Guillain-Bare syndrome. Recently, arteriosclerosis and Alzheimer's disease have been recognized as autoimmune diseases. Thus, in this embodiment of the invention the subject CD27 agonist, typically an agonistic CD27 antibody may be administered alone or in combination with a self-antigen against which the host elicits an unwanted immune response that contributes to tissue destruction and the damage of normal tissues.

The subject anti-CD27 antibodies and combination therapies can also be used to treat asthma and allergic and inflammatory diseases. Asthma is a disorder of the respiratory system characterized by inflammation and narrowing of the airways and increased reactivity of the airways to inhaled agents. Asthma is frequently although not exclusively associated with atopic or allergic symptoms. Allergy is acquired hypersensitivity to a substance (allergen). Allergic conditions include eczema, allergic rhinitis, or coryza, hay fever, bronchial asthma, urticaria, and food allergies and other atopic conditions. An allergen is a substance that can induce an allergic or asthmatic response in a susceptible subject. There are numerous allergens including pollens, insect venoms, animal dander, dust, fungal spores, and drugs.

Examples of natural and plant allergens include proteins specific to the following genera: *Canine, Dermatophagoides, Felis, Ambrosia, Lotium, Cryptomeria, Alternaria, Alder, Alinus, Betula, Quercus, Olea, Artemisia, Plantago, Parietaria, Blatella, Apis, Cupressus, Juniperus, Thuya, Chamaecyparis, Periplanet, Agopyron, Secale, Triticum, Dactylis, Festuca, Poa, Avena, Holcus, Anthoxanthum, Arrhenatherum, Agrostis, Phleum, Phalaris, Paspalum, Sorghum,* and *Bromis.*

It is understood that the subject antibodies, antibody containing compositions, and conjugates thereof can be combined with other therapies for treating the specific condition, e.g., infectious disease, cancer or autoimmune condition. For example in the case of cancer the inventive methods may be combined with chemotherapy or radiotherapy.

Methods of making antibodies against desired antigens are well known. However, until the present invention, agonistic CD27 mAbs have not been reported.nor has the use thereof for immune therapy been suggested as claimed herein.

By contrast, as noted above agonistic CD40 antibodies are known as is the use thereof in immune therapies. Variable sequences for the heavy and light chain of a preferred exemplary chimeric agonistic CD40 antibody LOB 7/4 may be used make this antibody by recombinant methods. If the CD27 antibody is used in association with a CD40 agonistic antibody, the effective amounts of the subject CD40 agonist and CD27 agonist can be determined empirically, or based on immunologically effective amounts in animal models. The relative amounts are those which result in an enhanced CTL response and proliferation of CD8+ T cells in vivo. Additional factors to be considered include the antigenicity, the formulation, the route of administration, the number of immunizing doses to be administered, the physical condition, weight, and age of the individual, adverse effects and the like. Such factors are well known to those skilled in the art and can be determined by those skilled in the art (see for example Paoletti and McInnes,eds., Vaccines, from Concept to Clinic: A Guide to the Development and Clinical Testing of Vaccines for Human Use CRC Press (1999)). It is understood that the subject CD27 agonist can be administered alone or in conjunction with other adjuvants.

The subject agonist or combination thereof, e.g., CD40/CD27 agonistic antibody combination, can be administered locally or systemically by any method known in the art including but not limited to intramuscular, intravenous, intradermal, subcutaneous, intraperitoneal, intranasal, oral or other mucosal routes. Additional routes include intracranial (for example intracisternal, or intraventricular), intraorbital, ophthalmic, intracapsular, intraspinal, and topical administration. The adjuvants and vaccine compositions of the invention can be administered in a suitable, nontoxic pharmaceutical carrier, or can be formulated in microcapsules or a sustained release implant. The immunogenic compositions of the invention can be administered multiple times, if desired, in order o sustain the desired cellular immune response. The appropriate route, formulation, and immunization schedule can be determined by one skilled in the art.

In the methods of the invention, in some instances the antibody or antibody conjugate combination may be administered in conjunction with one or several antigens or other active agents, e.g., a cytokine or chemotherapeutic. These compositions and active agents containing may be administered separately or in combination in any order that achieve the desired enhancement of cellular immunity. Typically, these compositions are administered within a short time of one another, i.e. within about a day of one another, typically several hours of one another, and more typically within about an hour or less of each other.

In some instances, it may be beneficial to include a moiety on the recombinant antibody agonist which facilitates affinity purification. Such moieties include relatively small molecules that do not interfere with the function of the polypeptides in the conjugate. Alternatively, the tags may be removable by cleavage. Examples of such tags include polyhistidine tags, hemagglutinin tags, maltase binding protein, lectins, glutathione-S transferase, avidin and the like. Other suitable affinity tags include FLAG, green fluorescent protein (GFP), myc, and the like.

The subject antibodies and antibody conjugates containing can be administered with a physiologically acceptable carrier such as physiological saline. The composition may also include another carrier or excipient such as buffers, such as citrate, phosphate, acetate, and bicarbonate, amino acids, urea, alcohols, ascorbic acid, phospholipids, proteins such as serum albumin, ethylenediamine tetraacetic acid, sodium chloride or other salts, liposomes, mannitol, sorbitol, glycerol and the like. The agents of the invention can be formulated in various ways, according to the corresponding route of administration. For example, liquid formulations can be made for ingestion or injection, gels or procedures can be made for ingestion, inhalation, or topical application. Methods for making such formulations are well known and can be found in for example, "Remington's Pharmaceutical Sciences," $18^{th}$ Ed., Mack Publishing Company, Easton Pa.

The subject agonistic antibodies can be expressed using any vector capable of directing its expression, for example a cell transduced with the vector. Vectors which may be used include by way of example baculovirus, T7 based vectors for use in bacteria, yeast expression vectors, mammalian expression vectors, viral expression vectors, and the like. Viral vectors include retroviral, adenoviral, adeno-associated vectors, herpes virus, simian virus 40, and bovine papilloma virus vectors.

Prokaryotic and eukaryotic cells that can be used to facilitate expression of the subject agonistic antibodies include by way of example microbia, plant and animal cells, e.g., prokaryotes such as *Escherichia coli, Bacillus subtilis*, and the like, insect cells such as Sf21 cells, yeast cells such as *Saccharomyces, Candida, Kluyveromyces, Schizzosaccharomyces*, and *Pichia*, and mammalian cells such as COS, HEK293, CHO, BHK, NIH 3T3, HeLa, and the like. One skilled in the art can readily select appropriate components for a particular expression system, including expression vector, promoters, selectable markers, and the like suitable for a desired cell or organism. The selection and use of various expression systems can be found for example in Ausubel et al., "Current Protocols in Molecular Biology, John Wiley and Sons, New York, N.Y. (1993); and Pouwels et al., Cloning Vectors: A Laboratory Manual", 1985 Suppl. 1987). Also provided are eukaryotic cells that contain and express the subject DNA constructs.

As used herein, the term "antibody" is used in its broadest sense to include polyclonal and monoclonal antibodies, as well as antigen binding fragments thereof. This includes Fab, F(ab')$_2$, minibodies, single chain Ab and Fv fragments.

In addition the term "antibody" includes naturally antibodies as well as non-naturally occurring antibodies such as single chain antibodies, chimeric antibodies, bifunctional and humanized antibodies. Preferred for use in the invention are chimeric, humanized and fully human antibodies. Methods for synthesis of chimeric, humanized, CDR-grafted, single chain and bifunctional antibodies are well known to those skilled in the art. In addition, as noted antibodies specific to CD27 are known and available and can be made by immunization of a suitable host with a CD27 antigen, preferably human CD27 antigen. As noted in the present invention if a CD40 antibody is used the CD40 antibody may comprise chimeric LOB 7/4 having variable heavy and light chain sequences.

The agonistic CD27 antibodies of the present invention may be intact or engineered For example, the CD27 mAb may be fully or partially glycosylated and/or selected for increased or diminished binding to human effector systems such as complement, FcR-bearing effectors, such as macrophages, or to extend or reduce half-life. These modifications can be made to improve effectiveness and potentially also reduce toxic side effects.

It is understood that modifications which do not substantially affect the activity of the various embodiments of this invention are also provided within the definition of the invention provided herein. Accordingly, the following examples are intended to illustrate but not limit the present invention.

EXAMPLES

Materials and Methods (The following materials and methods were used in Examples 1-6.)

Animals and cell lines BALB/c and C57B1/6 mice were supplied by Harlan (Blackthorn, Oxon, U.K.) and maintained in local animal facilities. The BCL1 (Slavin and Strober 1978) mouse B lymphoma line was maintained by in vivo by i.p. passage in BALB/c mice. Spleens were removed at the terminal stage of disease and single cell suspensions were prepared as described previously. P BCL1 cells are a subline derived from BCL1 and grow in culture (Illidge, Honeychurch et al. 2000). Animal experiments were conducted under license according to the U.K. Home Office license guidelines and approved by the University of Southampton Ethical Committee.

Antibodies and reagents The anti-CD40 treatment mAb used in this study was 3/23 (originally provided by G. Klaus, National Institute of Medical Research, London, U.K.). The anti-4-1BBL mAb, AT113-2, and the anti-CD70 mAb TAN1-6 (Taraban, Rowley et al. 2004) were raised in house by immunizing rats with 4-1BBL-Fc fusion protein or soluble recombinant CD70 protein respectively. For the preparation of mAb, hybridoma cells were expanded in stationary culture and IgG prepared from supernatant using Protein G-coupled Sepharose beads. Antibodies used for flow cytometric analysis were: ID3 (anti-CD19) (Krop, de Fougerolles et al. 1996) 16-10A1 (anti-B7-1) and GL-1 (anti-B7-2) (both American Type Culture Collection), ICAM-1 (ref), N418 (anti-CD11c) (ATCC), Mc10-6A5 (anti-BCL1 Id mAb) (George, McBride et al. 1991), LOB12/3 (anti-4-1BB) (Taraban, Rowley et al. 2004), YTS169 (anti-CD8), all prepared and PE- or FITC-labeled in house; PE-labeled anti-CD27 and APC-labeled anti-CD8 (both Pharmingen). Soluble fusion proteins, sCD70-Fc and s4-1BBL-Fc, were generated as described previously (Rowley and Al-Shamkhani 2004).

BIACORE Analysis Biacore analysis of the binding of TAN1-6 and AT113-2 was performed as described previously (Al-Shamkhani, Mallett et al. 1997).

Adoptive Transfer of OT-1 cells OVA-specific H-2 Kb-restricted TCR transgenic T cells (1×106) from OT-I mice were injected i.v. into sex-matched C57BL/6 recipients. After 1 or 2 days, T cells were primed by i.p. administration of OVA (5 mg) in combination with: anti-CD40 or control anti-A31 lymphoma Id mAb (500 μg of each), or anti-CD40 and anti-CD70/anti-4-1BBL mAb (500 μg of each). The next day these mice received an additional injection of control anti-A31 lymphoma Id mAb, anti-CD70 or anti-4-1BBL mAb (500 μg). For tracking Ag-specific T cells, blood samples (50 μl), were stained with PE-labeled H-2 Kb OVAp tetramers (Proimmune or Beckman Coulter) and APC-labeled anti-CD8 (Pharmingen) (Taraban, Rowley et al. 2004).

Monitoring of endogenous anti-OVA response C57BL/6 mice were primed by i.p. administration of OVA (5 mg) in combination with anti-CD40 and either control (anti-A31 lymphoma Id), anti-CD70 or anti-CD137L mAb (500 μg of each). The next day mice received an additional injection of either control, anti-CD70 or anti-CD137L mAb (500 μg). For tracking Ag-specific T cells, 6 days after priming, blood samples (50 μl), were stained with PE-labeled H-2 Kb OVAp tetramers and APC-labeled anti-CD80) (Pharmingen), and flow cytometric analysis was performed using a FACSCalibur (BD Biosciences, Mountain View, Calif.).

Flow cytometric analysis of splenic lymphocytes and DCs following tumor and anti-CD40 mAb Age-matched BALB/c mice were given 5×107 BCL1 cells on day 0 (i.v.) and then 1 mg of anti-CD40 mAb or isotype-matched control (i.v.) when the level of tumor cells in the spleen had reached approximately 5% of total cells, typically day 4 post-tumor. In experiments to look at the effect of anti-4-1BBL and anti-CD70 mAb on the response of anti-CD40 mAb treatment, 0.5 mg of the blocking mAb was injected i.p. 4 h prior to the injection of anti-CD40, and then again on days 1 and 3 after the anti-CD40 mAb. Animals were sacrificed on the days indicated, spleens removed and suspensions prepared. BCL1 tumor cells were detected using PE-anti-CD19 and FITC-anti-BCL1 Id. Changes in number and phenotype of CD8+ lymphocytes were followed using APCanti-CD8a and PE-anti-4-1BB and -anti-CD27. Flow cytometric analysis was performed using a FACSCalibur (BD Biosciences).

For DC analysis, whole spleens were coarsely chopped and digested in 5 ml of 1 mg/ml collagenase D (Roche) and 0.05 mg/ml DNaseI (Sigma) in RPMI-1640 and gently agitated for 30 min at 37 degrees C. 20 ml of medium was then added and a single cell suspension prepared. The cells were washed once, resuspended, and samples labeled for flow cytometry using PE-anti-CD11c and FITC-anti-B7.1, B7.1, ICAM, 4-1BB, 4-1BBL, and CD70 in the presence of the anti-FcgII and III receptor mAb, 2.4G2. 7-aminoactinomycin-D (7AAD) at a final concentration of 2 µg/ml was added to the samples 15 minutes before analysis so that dead and autofluorescent cells could be gated out using FL3. Flow cytometric analysis was performed using a FACSCalibur.

Immunotherapy Groups of 5 age-matched mice were injected i.v. with 107 BCL1 cells on day 0 and then with anti-CD40 i.v. on days 4 to 7 (250 mg/day) and blocking mAb i.p. on days 4, 7, 9 and 11 (500 mg/day) where indicated.

In vivo killing assay Mice were injected with 2×107 BCL1 cells i.p., and 48 hours later with 1 mg anti-CD40 i.p. After 8 days, groups of three mice were injected i.p. with 1 mg of the appropriate blocking mAb and then 5 hours later with 2×107 CFSE labeled splenocytes from terminal BCL1 tumor-bearing mice. Twenty four hours later, cells were harvested from the peritoneal cavity by washing and staining with PE-labeled anti-BCL1 Id and APC-labeled anti-CD8.

Cytotoxicity assay A standard 4-h 51Cr release assay was used to assess cytotoxic activity of splenic effectors as described previously (Tutt, O'Brien et al. 2002). Briefly, splenic homogenates were prepared from BCL1-bearing mice 4-5 days after anti-CD40 treatment. Remaining tumor cells were removed using FITC-anti-Id mAb, followed by anti-FITC MACS beads and LS columns (Miltenyi Biotec, Bergisch Gladbach, Germany). The remaining cells were used as effectors. PBCL1 cells were labeled with 51Cr and used as targets. To assess the effect of mAb on cytotoxicity, they were included at a final concentration of 50 µg/ml. The maximum release of radioactivity was calculated using target cells to which 150 µl of 1% Nonidet P-40 had been added. The percentage of specific 51Cr release was calculated using the standard formula: percentage of specific release=[(sample release−background release)/(maximum release−background release)]×100.

Example 1

Figure 1B:
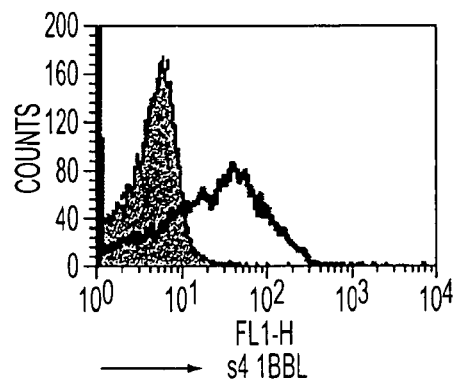

TAN1-6 (ANTI-CD70) and AT113-2 (Anti-4-1BBL) Block the 4-1BBL/4-1BB and CD70/CD27 Interactions Respectively In Vitro and In Vivo In this experiment contained in FIG. 1, in both 1a and 1b BALB/c splenocytes were activated for 48 hours with 1 microgram/ml of anti-CD3 to up-regulate the expression of CD70 and 4-1BB on T cells. In 3a, the binding of sCD70-IgFc fusion protein (1.125 micrograms/ml) to the activated splenocytes was detected using the FITC-labeled anti-human Fc mAb (SB2H2, 10 micrograms/ml) in the presence of s4-1BBL-Ig Fc fusion protein (1.125 micrograms/ml) to the cells was detected using the FITC-labeled anti-human Fc mAb SB2H2 in the presence of TAN1-6 (solid line) or AT113-2 (dashed line) (50 micrograms/ml). In both a and 1b the filled histograms show a control of hIgG detected with SB2H2. In 1c, the endogenous Ova-specific CD8 T-cell response in C57B1/6 mice was monitored following i.p. administration of OVA (5 mg) and anti-CD40 (1 mg) in combination with either control IgG (anti-A31 idiotype), anti-CD70 (TAN1-6) or anti-4-1BBL (AT113-2) mAb (0.5 mg of each). After 24 hours, the mice received repeated injection of control, anti-CD70 or anti-4-1BBL mAb. Six days later, the OVA-specific T cells in the peripheral blood were detected with APC-labeled anti-CD8 and PE-labeled H-2 Kb SIINFEKL tetramer.

Example 2

Figure 2:
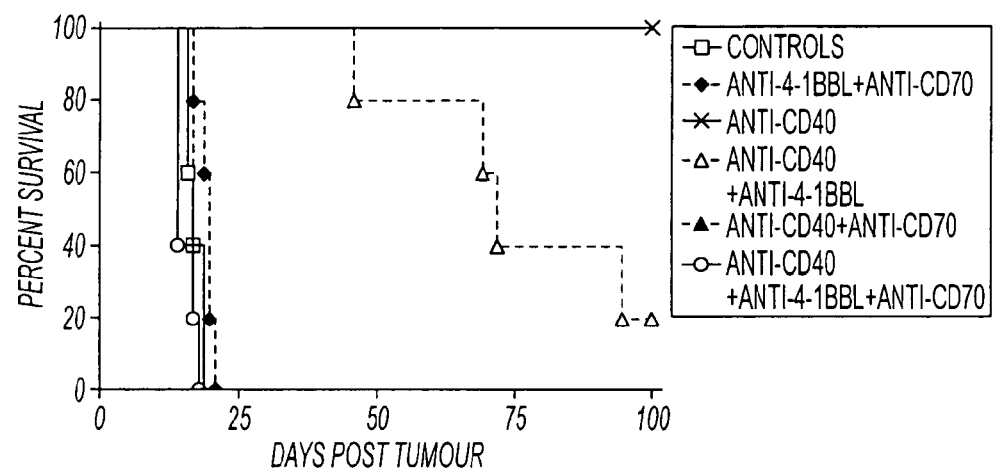
FIG. 2 contains the results of an experiment that shows the effect of anti-4-1BBL (AT113-2) and anti-CD70 (TAN1-6) on the therapeutic activity of anti-CD40 in BCL1 mice.
Figure 4A:
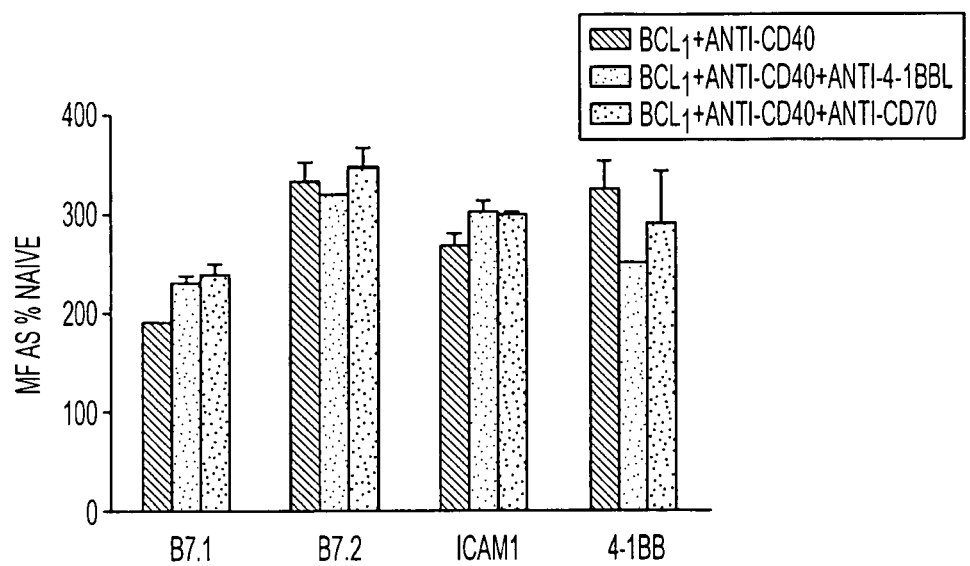
FIG. 4 contains the results of an experiment that shows that anti-4-1BBL (AT113-2) and anti-CD70 (TAN1-6) do not affect the anti-CD40 induced phenotypic changes or changes in the number of splenic DCs from BCL1 mice.
Figure 4B:
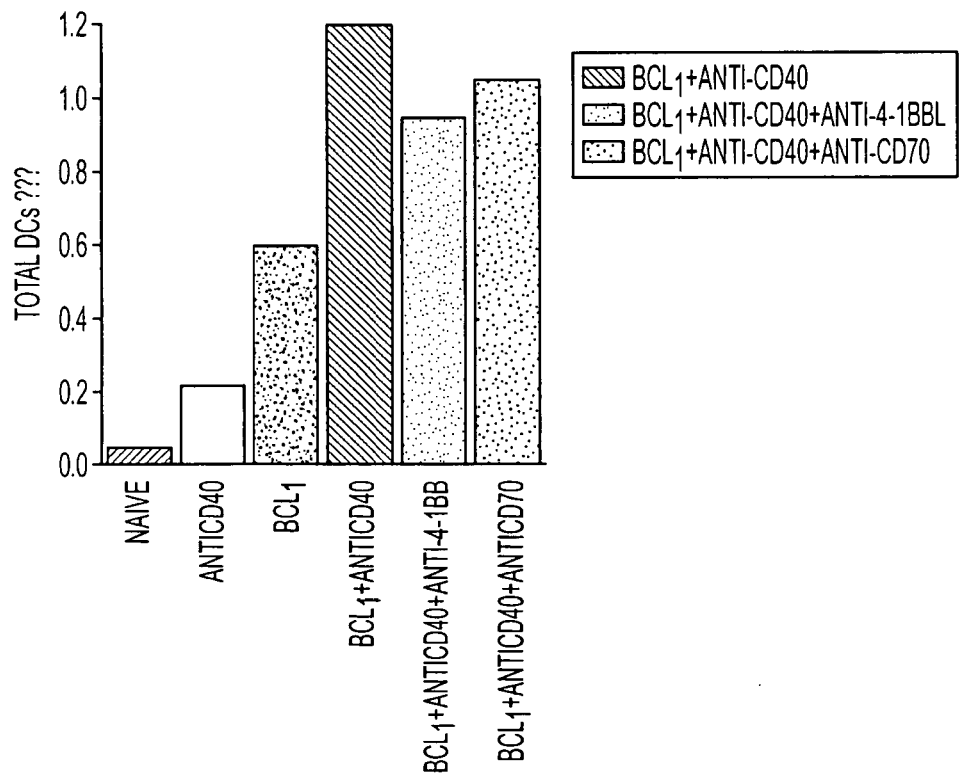

Effect of Anti-4-1BBL (AT113-2) and Anti-CD70 (TAN1-6) on the Therapeutic Activity of Anti-CD40 in BCL1 Mice In this experiment shown in FIG. 2, groups of 5 mice were inoculated iv with 1×107 BCL1 tumor cells o day 0, and treated iv with anti-CD40 on days 4, 5, 6 and 7 post-tumor (500 micrograms per day). Where shown, the groups also received anti-4-1BBL and/or anti-CD70 on days 4, 7, 9 and 11 (500 micrograms/mAb/day, i.p. Mice were monitored for tumor development. These results in FIG. 4 represent and contain the results of one of 3 similar experiments.

Example 3

Figure 3A:
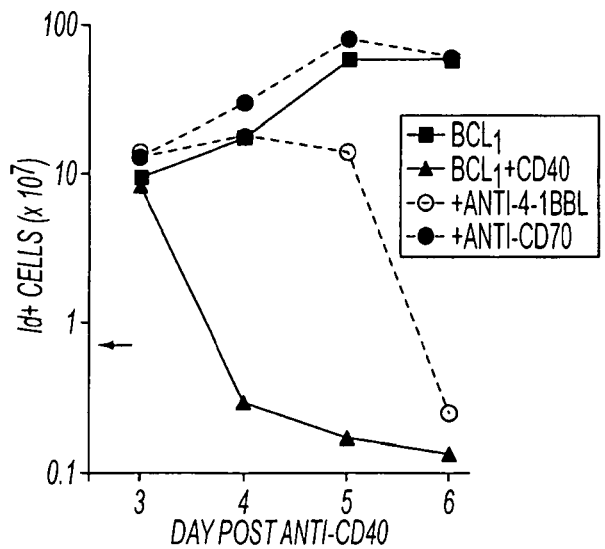
FIG. 3 contains the results of an experiment showing the effect of anti-4-1BBL and anti-CD70 on the accumulation of CD8+ T cells and the eradication of BCL1 tumor after anti-CD40 mAb therapy.

Effect of Anti-4-1BBL and Anti-CD70 on the Accumulation of CD8+ T Cells and The Eradication of BCL1 Tumors After Anti-CD40 mAb Therapy In this experiment the results of which are contained in FIG. 3, groups of mice were inoculated with 5×107 BCL1 cells iv and four days later (day 0 in the figure) treated with anti-CD40 mAb, at which point the level of Id+-tumor cells in the spleen was between 3 and 5%. Where indicated, the mice also received anti-4-1BBL and/or anti-CD70 mAb on days 0, 1, and 2 (500 micrograms/mAb/day). On the days indicated, splenic tumor and CD8+ T cells were monitored by flow cytometry as described in the Materials and Methods herein. The experiment in FIG. 3a shows the total number of splenic tumor cells and 3b the total numbers of CD8+ cells after treatment of BCL1. The points are the mean of duplicate animals, and the results shown represent the results of 4 similar experiments.

Example 4

Anti-4-1BBL (AT113-2) and Anti-CD70 (TAN1-6) Do Not Affect the Anti-CD40 Induced-Phenotype Changes or Changes in the Number of Splenic DCs from BCL1 Mice In the experiment in FIG. 4 mice were inoculated with 5×107 BCL1 cells iv and four days later (day 0 in the figure) treated with anti-CD40 (1 mg) mAb. Where indicated, the mice also received anti-4-1BBL or anti-CD70 i.p four hours prior to anti-CD40 treatment, and again 1 and 2 days later (500 micrograms/day). On day three, the total number of splenic DCs were analyzed as in FIG. 2. The results in FIG. 4 represent the means of duplicate mice and contain the results of 1 of 2 similar experiments.

Example 5

Figure 5A:
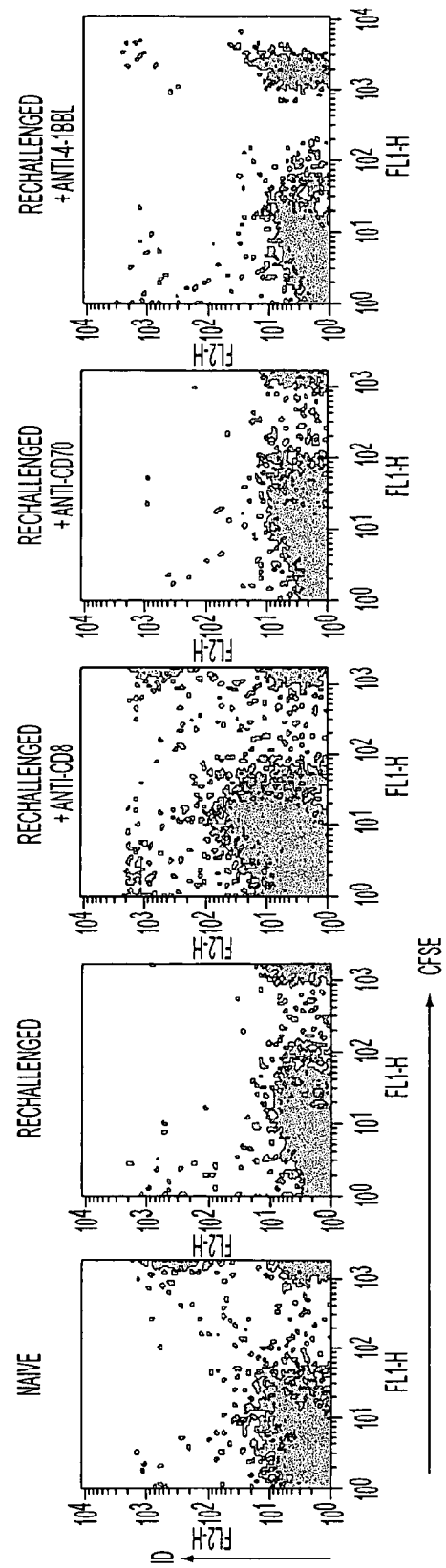
FIG. 5 contains the results of an experiment that shows that anti-4-1BBL and anti-CD70 antibodies do not inhibit the effector stage of the response in vivo or in vitro.
Figure 5B:
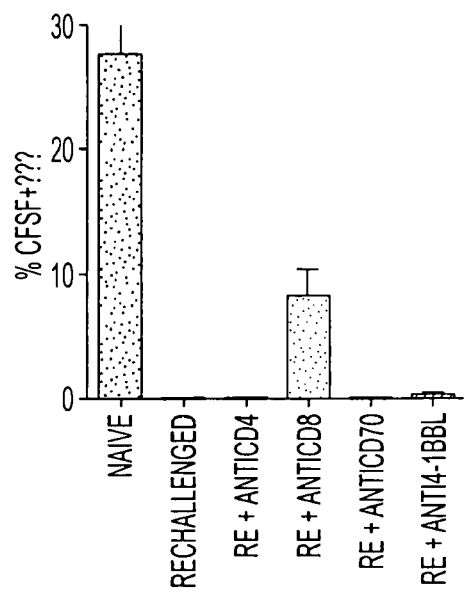

Anti-4-1BBL and Anti-CD70 Do Not Inhibit the Effector Stage of the Response In Vivo or In Vitro This experiment is contained in FIG. 5. In FIG. 5a mice were given. i.p. injections of 2×107 BCL1 cells and 48 hours later anti-CD40 mAb (1 mg). After an additional 8 days, groups of three mice were injected i.p. with 1 mg of the appropriate blocking antibody and then 5 hours later with $2\times10^7$ CFSE labeled splenocytes from BCL1 tumor-bearing mice. 24 hours later, cells were harvested from the peritoneal cavity, stained with PE-labeled anti-BCL1 Id, and evaluated by flow cytometry. The gated, double positive (CFSE+ and Id+) cells represent the surviving tumor cells. In 5b) mice were inoculated with $5\times10^7$ BCL1 i.v. and treated 4 days late with anti-CD40 mAb (1 mg, i.v.). 5 days after anti-CD40, splenic lymphocytes were prepared and the remaining tumor cells, removed using PE-labeled anti-BCL1 Id mAb and anti-PE beads as describe in the Material and Methods. The remaining splenocytes (approximately 40% CD8+) were used as effectors, and incubated with 51 Cr-labeled IIBCL1 cells as targets, alone, or in the presence of anti-CD40, anti-CD8, anti-4-1BBL, or anti-CD70 at 100 micrograms/ml. The results therein are expressed as the percentage specific lysis of target cells.

Example 6

Therapeutic Potency of Anti-CD27 Against A31 and BCL1 Lymphoma

Figure 6:
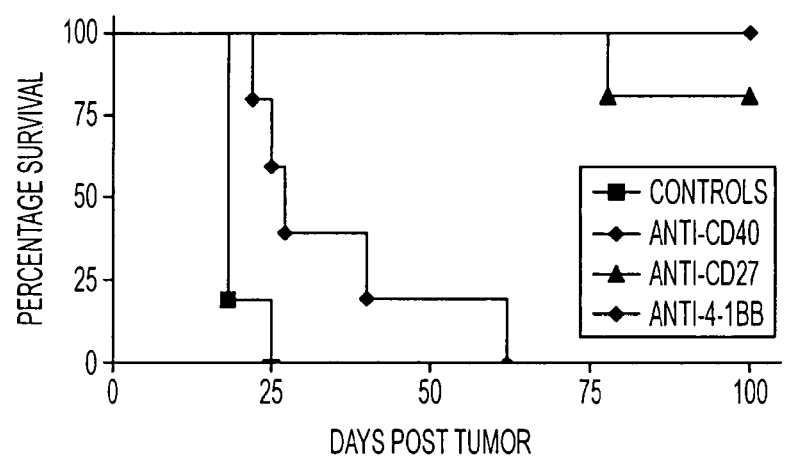
FIG. 6 contains the results of an experiment that demonstrates the therapeutic efficacy and potency of agonistic CD27 monoclonal antibodies against two B cell lymphomas (BCL1 and A31).

In this experiment shown in FIG. 6, mice were given injections of $2\times10^7$ BCL1 cells iv and then later treated iv with Control IgG, anti-CD40 mAb, anti-CD27 or anti-4-1BB mAb (1 mg). The mice were monitored twice daily and the results in the figure represent one of two similar experiments. Particularly, one day after adoptive transfers of $4\times10^6$ CD8+ OT-I lymphocytes (day 0), the recipient B6 mice were immunized iv with 30 mmol OVA peptide (SINFEKL, OVA 257-264). The animals also received four iv injections (on days 90, 1, 2 and 3; 250 micrograms per injection) of recombinant soluble CD70 or anti-mouse CD27 (preparation thereof described in the next example) or control mAb. For tracking of OVA-specific CD8+ T cells in vivo, blood samples were stained with PE H-2 KB OVA 257-264 tetramer and APC anti-CD8alpha. Expansion of OVA-specific CD8+ T cells is shown on day 4, at the peak of the response.

Example 7

Preparation of Anti-Mouse CD27 mAb AT124-1

Mouse CD27-huFc secreting CHO cells were prepared and supernatant therefrom processed over Protein A to purify the fusion protein. Lou rats were immunized with 50 micrograms/dose fusion protein in CFA, IFCA, then PBS following standard methods. Hybridomas were screened initially on the fusion protein and subsequently on the cells. The cells were Con A activated spleen cells, i.e., activated T cells.

Compared to commercial Hamster CD27 (LG3A10 (Becton Dickinson) P 04 2 115), AT124-1 (inventive antibody) was partially or was not blocked by CD70-Fc (110 down to 80 MFI) whereas LG3A10-PE was blocked 1500 down to 180 MFI. This experiment was repeated with P 04 2 130 with similar results.

Figure 7:
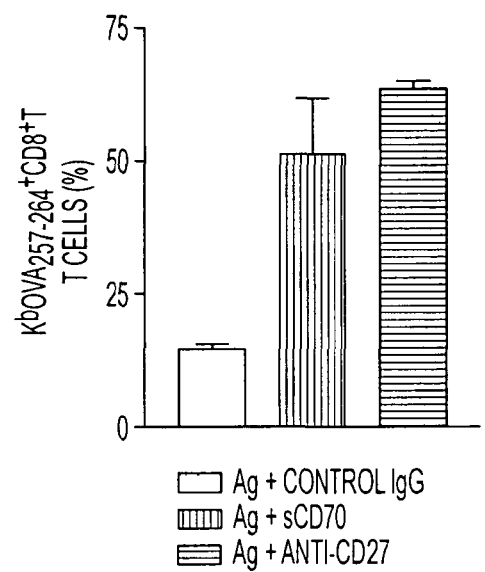
FIG. 7 contains experiments that show that the anti-CD27 mAb elicits a stronger response (higher and longer) in OT-I cells than the CD70 ligand. The figure shows the expansion of Ag-specific (OT-1) cells in mice given Ag+ control Ab, Ag+ soluble recombinant CD70 or an agonistic CD27 antibody according to the invention. The results in the figure show substantial expansion of CD8+ OT-1 with the agonistic CD27 mAb. (See Example 6)
Figure 8A:
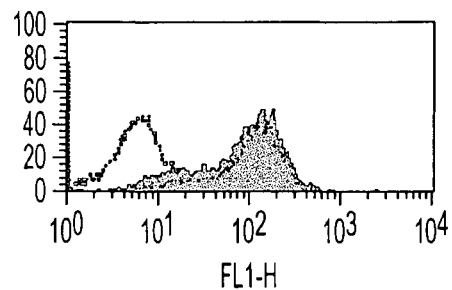
FIG. 8 shows mouse CD27 transiently expressing cells labeled with anti-mouse CD27 antibodies. As shown therein both the test anti-rat anti-mouse CD27 (AT124-1) and positive control hamster anti-mouse CD27 (LG3A10) labeled the mouse transfected cells. Neither antibody bound to non-transfected cells (data not shown).
Figure 8B:
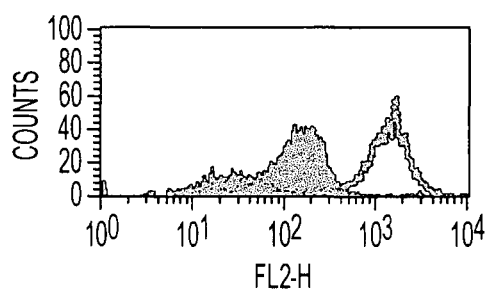
Figure 9A:
FIG. 9 shows blocking of CD70 and CD27 with the anti-CD27 mAb. This figure shows that AT 124-1 binds to CD27 on the surface of activated mouse T cells and that this binding is not inhibited by the interaction of CD27 with its natural ligand CD70. By contrast, the comparison commercially available anti-CD27 antibody (LG3A10; a non-agonist) was shown to compete for binding with CD70.
Figure 9B:
Figure 9C:
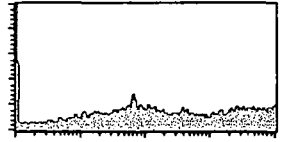
Figure 9D:
Figure 9E:
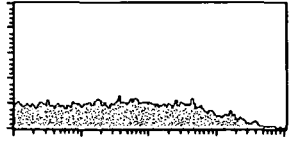
Figure 9F:
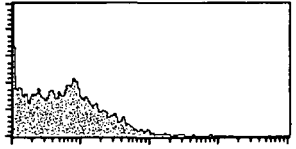
Figure 9G:
Figure 9H:
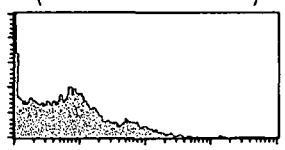

As shown in FIG. 7 both the inventive rat anti-mouse CD27 (AT124-1) and the positive control hamster anti-mouse CD27 (LG3A10) labeled the mouse CD27 transfected cells. Neither antibody bound untransfected cells.

Results

Phenotypic changes in splenic CD8 T cells and DC during anti-CD40 treatment of BCL1 lymphoma Effect of blocking 4-1BBL/4-1BB and CD70/CD27 interactions on the therapeutic response to anti-CD40

Figure 1C:
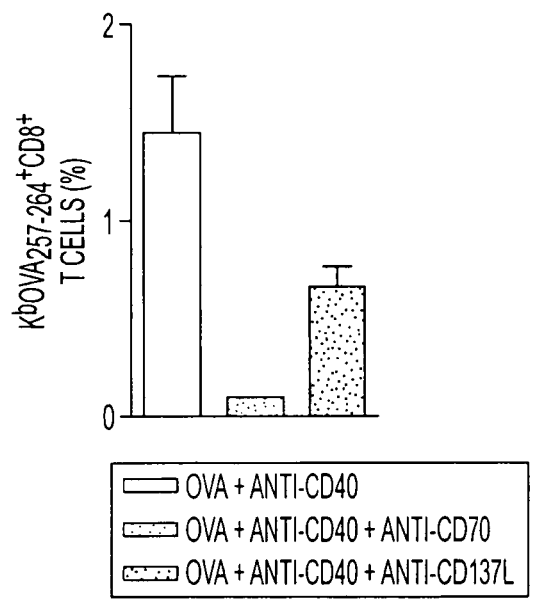

The inventors investigated the importance of the 4-1BB and CD27 molecules to the therapeutic response seen following CD40 mAb treatment of tumor-bearing mice. The effect of disrupting 4-1BBL/4-1BB and CD70/CD27 interactions was investigated using blocking mAb specific for 4-1BBL and CD70. That AT113-2 (anti-4-1BBL) and TAN1-6 (anti-CD70) were able to disrupt 4-1BBL/4-1BB, and CD70/CD27 interactions respectively, was confirmed by showing that they blocked the binding of s4-1BBL-Fc and sCD70-Fc to activated T cells (FIGS. 1a and b). Furthermore, both mAb bound to their target antigens with similar affinity as determined by BIACore analysis. The KD values for AT113-2 (anti-4-1BBL) and TAN1-6 (anti-CD70) were $3.8\times10^{-9}$ and $3.0\times10^{-9}$ respectively. To confirm that the anti-CD70 and anti-4-1BBL mAb were able to block responses in vivo, the inventors investigated their effect on the endogenous CD8 response to OVA in C57BL/6 mice (FIG. 1c). As shown previously (Taraban, Rowley et al. 2004), the CD40 mediated expansion of endogenous OVA-specific CD8 T cells was almost completely inhibited by anti-CD70 mAb. In comparison, the anti-4-1BBL mAb resulted in a 50% reduction in the level of anti-CD40 induced OVA-specific T cells.

The inventors then determined the effect of the anti-CD70 and anti-4-1BBL mAb on the therapeutic response of BCL1 tumor bearing mice to anti-CD40 mAb. Mice were inoculated with $1\times10^7$ BCL1 tumor cells i.v. on day 0, and treated with anti-CD40 on days 4, 5, 6 and 7 post tumor. FIG. 2 shows that, as we have previously reported (French, Chan et al. 1999; Tutt, O'Brien et al. 2002) BCL1-bearing mice treated with anti-CD40 are protected against lymphoma and go on to become long-term survivors (survived more than 100 days). However, CD70 mAb completely blocked the therapeutic activity of the CD40 mAb treatment. In contrast, mice receiving the blocking 4-1BBL mAb survived for a median of 73 days, compared with 18 days for the untreated group, and then succumbed to disease, suggesting some impairment in the development of long-term immunity in the absence of 4-1BB co-stimulation. The inventors consistently found that CD40 mAb-treated mice receiving both anti-4-1BBL and anti-CD70 succumbed to tumor slightly earlier than control untreated animals (median survival 14 days compared with 17 days), suggesting that this combination might block the CD40 mAb therapeutic activity and also perhaps a weak spontaneous response to the tumor.

Figure 3B:
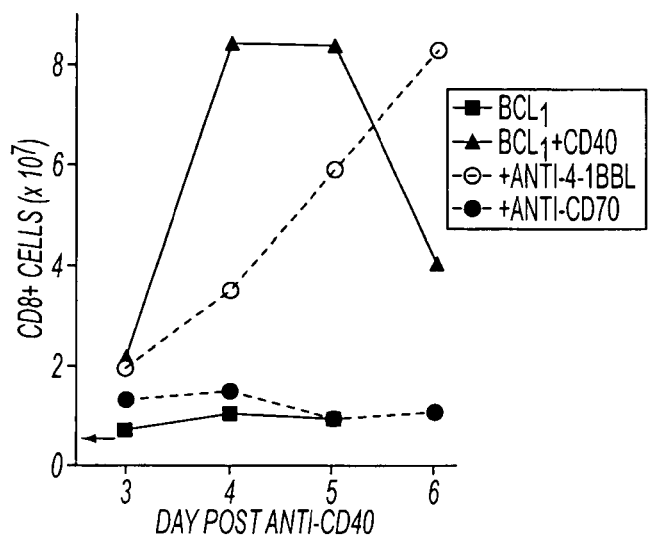

The inventors next investigated the effects of blocking with anti-4-1BBL and anti-CD70 mAb on the kinetics of the CD8 response to CD40 mAb treatment. FIG. 3 shows the effects of the 4-1BBL and anti-CD70 mAb on the growth of BCL1 (FIG. 3a) and the CD8 T-cell response (FIG. 3b) in the spleen of CD40 mAb-treated mice. Compared to CD40 mAb alone, treatment with CD40 mAb in the presence of anti-4-1BBL resulted in a delay in the expansion of CD8 T-cell of about 2 days resulting in the slower clearance of tumor cells from the spleen. However, although delayed, the final number of CD8 cells was at least as high as with anti-CD40 alone. Interestingly, in these experiments, where the initial tumor dose was $5\times10^7$ cells, rather than the $1\times10^7$ cells used in most immunotherapy experiments, mice treated with CD40 mAb and blocking 4-1BBL mAb went on to become long-term survivors and were immune to re-challenge with tumor (results not shown).

In contrast, anti-CD70 mAb completely blocked the anti-CD40-induced eradication of tumor cells. This lack of response was reflected in the failure of the CD8+ T cell population to expand and explains the ability of CD70 mAb to completely block the CD40 mAb-mediated therapy of BCL1 tumor shown in FIG. 2. The results demonstrate that the blocking of anti-CD70/anti-CD27 interactions has a profound effect on the therapeutic response. By contrast, the influence of the 4-1BBL/4-1BB interaction appears relatively modest.

Since it was observed that both anti-4-1BBL and anti-CD70 had an effect on the CD40 mAb-induced CD8 response (not shown) the inventors further assessed whether they were having any effect on the anti-CD40 induced changes in DC number and phenotype in tumor-bearing mice. As shown in FIG. 4, neither anti-4-1BBL nor anti-CD70 inhibited the increase in expression of B7.1, B7.2 and ICAM (a) or in the number of DC recovered (b) after anti-CD40 treatment of tumor-bearing mice. Thus blocking of these co-receptors does not influence DC recruitment and is unlikely to affect their activation.

Figure 5C:
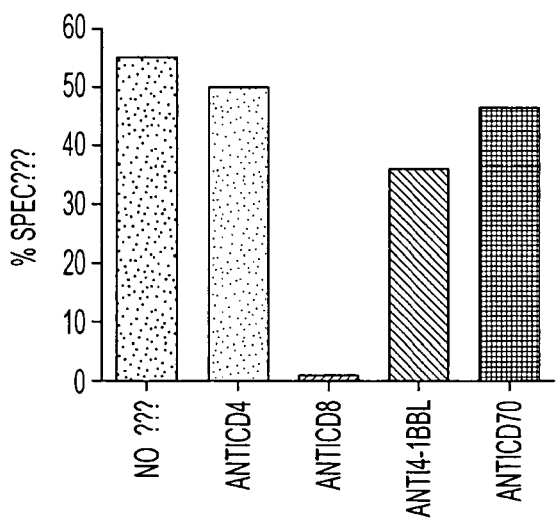

CD27 and 4-1BB do not operate at the effector stage of the CD40 mAb-mediated anti-tumor response Since we have observed that the BCL1 tumor cells themselves express both CD70 and 4-1BBL (FIG. 5a), and also since it has been reported that CD70 is also expressed by activated T cells (very recently by Steve Rosenberg), the inventors then investigated whether the anti-4-1BBL and anti-CD70 had an effect on the effector stage of the CTL response. It was observed (unpublished observations) that when BCL1 tumor cells are administered and treated with anti-CD40 mAb in the peritoneal cavity, then the CD8 response in that compartment peaks at day 8 post treatment, at which point approximately 30% of the recovered lymphocytes are CD8+ (5% in naïve mice), and clears the tumor rapidly. This system was used to investigate the effector stage of CTL-mediated killing in vivo. Mice received i.p. BCL1 and anti-CD40 mAb as described and then 8 days after anti-CD40 were injected i.p with 1 mg of anti-CD8, anti-CD4, anti-CD70 or anti-4-1BBL blocking mAb, or control PBS. Five hours later they were injected i.p. with 2×107 CFSE-labeled splenocytes from terminal BCL1-bearing mice as CTL targets. Labeled splenocytes were also injected into naïve mice as a comparison. Twenty four hours later, peritoneal cavity cells were harvested, and analyzed for the presence of CFSE labeled BCL1 tumor cells. The peritoneal cavity cells harvested from naïve mice included 22-27% CFSE-labeled tumor cells (FIG. 5). In contrast, tumor cells were completely eradicated in mice that had undergone anti-CD40 treatment of BCL1., underlining the effectiveness of this treatment. As expected, injection of anti-CD8 mAb blocked the clearance of CFSE-labeled tumor cells from the peritoneal cavity. However, anti-CD4, anti-4-1BBL and anti-CD70 had no effect on the clearance of transferred tumor cells. These results were confirmed in a cytotoxicity assay using splenocytes taken from BCL1-bearing mice 5 days after anti-CD40 treatment, after removal of residual tumor cells, as effectors, and the results are shown in FIG. 5c. Neither anti-4-1BBL nor anti-CD70 had a direct effect on the cytotoxicity of immune splenocytes.

Direct Immunotherapy via 4-1BB and CD27.

The results above suggest that the striking CTL response seen after tumor inoculation and CD40 mAb treatment, is partially dependent on triggering via 4-1BB and completely dependent on interactions between CD27 and CD70. Therefore, to investigate if we could short-cut the agonistic activity via CD40 and simulate these co-receptors directly, we next investigate the therapeutic potency of agonistic anti-4-1BB or anti-CD27 against the BCL1 lymphoma. As shown in FIG. 6, the anti-CD70 mAb was completely protective for BCL1 tumor and gave results which were very similar to those obtained with anti-CD40 mAb. In contrast the anti-4-1BB mAb had a modest therapeutic activity for this tumor, giving little prolongation of survival.

Agonistic CD40 mAb is one of the most exciting reagents currently under investigation for human use. For some time it has been known that, even as a monotherapy, anti-CD40 mAb has efficacy in a range of vaccine settings, including induction of tumor immunity in murine models and more recently in patients. For example, recent data from Vonderheide et al (2006) have shown that a fully human CD40 mAb can deliver PR in 27% of melanoma patients when given at close to its MTD (0.2 mg/kg).

While it is known that CD40 plays a critical role in the immune system, particularly in the activation of APC, such as DC, much is unknown about the role of co-receptor: ligand interaction between the activated DC and responding CTL. A wealth of evidence shows that triggering via CD40, such as that delivered with a mAb, activates the DC resulting in upregulation of MHC, B7.1/2, and various co-receptors and cytokines, to allow generation of effector CTL. Furthermore, it is generally found that using the appropriate CD40 agonist replaces the need for T-helper cells, and given the paucity of helper epitopes expressed by certain tumors, perhaps this explains the success of CD40 agonists in a cancer setting. In the subject current invention we have investigated the role of 4-1BBL and CD70, and shown how important signals via their respective receptors, 4-1BB and CD27, are in controlling CTL responses. Additionally, the inventors found that CD40 treatment promotes marked DC expansion and, as has been widely reported, an increase in the expression of I-CAM-1, B7.1 and B7.2 on splenic DC, consistent with their activation or 'licensing' for antigen presentation. It is generally accepted that the CD40 mAb-induced anti-tumor response is due to cross-presentation of tumor antigens by activated APCs (van Mierlo, Boonman et al. 2004). Consistent with this, we have previously shown that CD40 mAb therapy is at least partially effective with CD40-negative tumors (French, Chan et al. 1999). Splenic DC from mice receiving tumor alone showed a degree of activation, with partial up-regulation of B7.1, B7.2 and ICAM-1. However, somewhat surprisingly in view of the clear effect of both anti-CD70 and anti-4-1BBL on the CD40-induced response to lymphoma (FIG. 2), in spite of numerous attempts, only small and transient increases in the expression of CD70 and 4-1BBL were detected after anti-CD40 treatment, and even these were abrogated in the presence of tumor. Interestingly, 4-1BBL expression on in vitro activated DCs has also been shown to be low (DeBenedette, Shahinian et al. 1997; Futagawa, Akiba et al. 2002), although Diehl et al (Diehl, van Mierlo et al. 2002) have shown strong expression on splenocytes in response to anti-CD40 in vivo.

The low expression of 4-1BBL and CD70 on splenic DC in vivo, may reflect a transient expression of these two ligands or continual modulation by engagement of their receptors 4-1BB and CD27. Interestingly, we find that treatment of BMDC in vitro does promote CD70 expression, perhaps because it is not encountering CD27. While CD70 expression has been demonstrated on in vitro activated DCs (Futagawa, Akiba et al. 2002; Tesselaar, Xiao et al. 2003) (Taraban, Rowley et al. 2002; Bullock and Yagita 2005), in vivo expression of CD70 on DCs has generally been low and transient (Tesselaar, Xiao et al. 2003; Hendriks, Xiao et al. 2005), presumably to avoid inappropriate activation of T cells via the constitutively expressed CD27 (Tesselaar, Arens et al. 2003).

Despite this lack of CD70 expression, mAb against 4-1BBL or CD70 were effective in blocking the anti-tumor response and in the latter case the inhibition was complete.

Such blocking appeared to operate at the level of CTL stimulation, since while these blocking mAb prevented the generation of cytotoxic T cells, they had not effect on the number or activation of splenic DC, or on the cytotoxic function of the CD8 T cells once they had been generated. Together these studies show that 4-1BB and particularly CD27 are critical in controlling CTL responses during anti-CD40 mAb treatment, most likely to act at the level of the interaction between the DC and the responding CD8 T cells.

The expression of 4-1BB on CD8 T cells during the development of the CD40-induced anti-lymphoma response was consistent with the established pattern (Vinay and Kwon 1998; Takahashi, Mittler et al. 1999) with 4-1BB rapidly induced on the expanding CD40-induced splenic CTL population (FIG. 1), and then lost concomitant with the eradication of tumor cells, but before the contraction of the CTL population one to two days later (Tutt, O'Brien et al. 2002). The sustained expression of 4-1BB over 4 days during the response, presumably because of continuous antigen availability, resembles that found during persistent infection and graft rejection (Tan, Ha et al. 2000; Seo, Park et al. 2003). In untreated mice in the terminal stage of disease, the inventors identified a clear population of 4-1BB+CD8 T-cells, supporting the idea that BCL1 alone is able to evoke a weak, ineffectual T-cell response, which is then boosted to an effective level by treatment with CD40 mAb.

While 4-1BB is induced on T cells and there is evidence that it provides co-stimulation for T-cell proliferation (20), it is believed to impact primarily on cell survival (Takahashi, Mittler et al. 1999; Lee, Park et al. 2002), by inducing the expression of anti-apoptotic proteins (Lee, Park et al. 2002). Although the importance of 4-1BB in the development of CTL responses has been demonstrated in the allograft situation, where blockade of 4-1BB/4-1BBL interactions has been shown to result in the enhanced graft survival, with inhibition of the expansion of alloreactive T cells and reduced CTL activity (Cho, Kwon et al. 2004), studies in 4-1BB−/− and 4-1BBL−/− mice have shown only relatively minor impairment in primary CTL responses to virus infections (Tan, Whitmire et al. 2000; Bertram, Dawicki et al. 2004), with a more pronounced effect on the recall response after rechallenge (Dawicki and Watts 2004). Importantly, studies using agonistic anti-4-1BB mAb in vivo have shown that they are able to promote effective therapy in a range of poorly immunogenic tumor models (Wilcox, Flies et al. 2002) and that 4-1BB signaling is important predominantly during CD8 responses (Shuford, Klussman et al. 1997).

In contrast to 4-1BB, CD27 is constitutively expressed on naive T cells (Gravestein, Blom et al. 1993). Following anti-CD40 treatment of tumor, we were able to detect CD27-high and -low populations (FIG. 1c) in the expanding splenic CD8+ cells, possibly representing primed cells with a transient up-regulation of CD27 (Gravestein, Blom et al. 1993; Lens, de Jong et al. 1996) and a population of senescent terminal effectors as described by Kaech et al (Kaech, Tan et al. 2003) respectively. The expression of its ligand, CD70, on DC is tightly regulated, thus preventing inappropriate activation of T cells (Tesselaar, Arens et al. 2003). However, recently, constitutive triggering of CD27 by CD70 has been shown to enhance both the expansion and the activity of CD8+ cells in response to viral or tumor challenge (Arens, Schepers et al. 2004). We have recently shown that soluble CD70 promotes strong primary and secondary CTL responses in vivo (Rowley and Al-Shamkhani 2004). Conversely, CD27-deficient mice develop impaired CD8+ responses to influenza virus, and, like 4-1BB, CD27 appears to promote the survival of activated CD8+ T cells during the primary response (Hendriks, Gravestein et al. 2000; Hendriks, Xiao et al. 2003), but that, unlike 4-1BB, it is also important in CD4+ responses. The CD27-deficient mice also show an impaired response to rechallenge (Hendriks, Gravestein et al. 2000).

In addition to the well established idea that T cell expansion requires co-stimulation between ligands on DC and co-stimulatory receptors on T cells, the detection of these molecules on other cell types suggests a role for a more complex network of interactions during the T cell response. For example, CD70 has been detected on activated T cells (Borst, Hendriks et al. 2005; Hendriks, Xiao et al. 2005) and 4-1BB on activated DC both in vivo and in vitro. Although the inventors could not detect CD70 on activated T cell in our study, 4-1BB was clearly detected on activated DC during the course of the response (results not shown).

Finally, we confirmed was the relative importance of triggering via CD70 using an agonistic CD27 mAb as therapeutic agents for mouse lymphoma. The data herein show that CD27 mAb was as effective as CD40 mAb in developing tumor immunity. Ongoing work is investigating the mechanism of action of this mAb, which presumably works by stimulating the T cells directly. The total dependency of the anti-CD40 induced CD8 T-cell response in both the OVA and the BCL1 lymphoma models on CD70/CD27 interactions is consistent with the reported effects of the CD70:CD27 co-stimulatory pathway in studies using viral models. While the importance of 4-1BB/4-1BBL interactions in the development of CTL responses has been demonstrated in the allograft situation, where blockade of 4-1BB/4-1BBL interactions results in to enhanced graft survival (DeBenedette, Wen et al. 1999; Cho, Kwon et al. 2004), studies in 4-1BB−/− and 4-1BBL−/− mice have shown only relatively minor impairments in primary CTL responses to LCMV and influenza infections (Bertram, Dawicki et al. 2004) (Tan, Whitmire et al. 1999) (Hendriks, Xiao et al. 2005). The observation that 4-1BBL−/− mice showed a more severe defect in their response after immunization with a lipidated LCMV peptide (Tan, Whitmire et al. 2000) suggested that 4-1BB-co-stimulation is more critical where antigenic stimulation is weak or limiting. In contrast, CD27-deficient mice develop impaired CD8+ responses to influenza virus in the lung and draining lymph node, although, interestingly, anti-viral CD8 cell expansion in the spleen was relatively unaffected (Hendriks, Xiao et al. 2003) in this system. Both 4-1BB and CD27-deficient mice have been shown to demonstrate an impaired secondary response to viral rechallenge (Hendriks, Gravestein et al. 2000) (Dawicki and Watts 2004). While our experiments showed that the presence of anti-4-1BBL mAb did not prevent initial clearance of the tumor after anti-CD40 treatment, in our immunotherapy experiments, animals receiving anti-CD40 and anti-4-1BBL mAb did not go on to become long term survivors (FIG. 2), suggesting some impairment in the development of their long-term immunity. In summary, these results and the underlying conclusions based thereon enumerated supra suggest that mono- and combination therapies using agonistic CD27 antibodies, e.g., synergistic agonist combinations will provide a novel means of promoting Th1 immunity and CD8+ T cell proliferation and may be used in the treatment of cancer, infection, inflammation, allergy and autoimmunity and for promoting the efficacy of vaccines.

It is to be understood that the invention is not limited to the embodiments listed hereinabove and the right is reserved to the illustrated embodiments and all modifications coming within the scope of the following claims.

The various references to journals, patents, and other publications which are cited herein comprise the state of the art and are incorporated by reference as though fully set forth.

Al-Shamkhani, A., S. Mallett, et al. (1997). "Affinity and Kinetics of the Interaction between Soluble Trimeric OX40 Ligand, a Member of the Tumor Necrosis Factor Superfamily, and Its Receptor OX40 on Activated T Cells." J. Biol. Chem. 272(8): 5275-5282.

Bennett, S. R. M., F. R. Carbone, et al. (1998). "Help for cytotoxic-T-cell responses is mediated by CD40 signalling." Nature 393(6684): 478-480.

Carreno, B. M. and M. Collins (2002). "THE B7 FAMILY OF LIGANDS AND ITS RECEPTORS: New Pathways for Costimulation and Inhibition of Immune Responses." Annual Review of Immunology 20(1): 29-53.

Cella, M., D. Scheidegger, et al. (1996). "Ligation of CD40 on dendritic cells triggers production of high levels of interleukin-12 and enhances T cell stimulatory capacity: T-T help via APC activation." J. Exp. Med. 184(2): 747-752.

DeBenedette, M. A., A. Shahinian, et al. (1997). "Costimulation of CD28-T lymphocytes by 4-1BB ligand." J Immunol 158(2): 551-559.

DeBenedette, M. A., T. Wen, et al. (1999). "Analysis of 4-1BB ligand (4-1BBL)-deficient mice and of mice lacking both 4-1BBL and CD28 reveals a role for 4-1BBL in skin allograft rejection and in the cytotoxic T cell response to influenza virus." J Immunol 163(9): 4833-41.

Diehl, L., G. J. D. van Mierlo, et al. (2002). "In Vivo Triggering Through 4-1BB Enables Th-Independent Priming of CTL in the Presence of an Intact CD28 Costimulatory Pathway." J Immunol 168(8): 3755-3762.

French, R. R., H. T. C. Chan, et al. (1999). "CD40 antibody evokes a cytotoxic T-cell response that eradicates lymphoma and bypasses T-cell help." Nat Med 5(5): 548-553.

Futagawa, T., H. Akiba, et al. (2002). "Expression and function of 4-1BB and 4-1BB ligand on murine dendritic cells." Int. Immunol. 14(3): 275-286.

George, A. J., H. M. McBride, et al. (1991). "Monoclonal antibodies raised against the idiotype of the murine B cell lymphoma, BCL1 act primarily with heavy chain determinants." Hybridoma 10(2): 219-27.

Gravestein, L. A., B. Blom, et al. (1993). "Cloning and expression of murine CD27: comparison with 4-1BB, another lymphocyte-specific member of the nerve growth factor receptor family." Eur J Immunol 23(4): 943-50.

Hendriks, J., L. A. Gravestein, et al. (2000). "CD27 is required for generation and long-term maintenance of T cell immunity." Nat Immunol 1(5): 433-40.

Hendriks, J., Y. Xiao, et al. (2003). "CD27 promotes survival of activated T cells and complements CD28 in generation and establishment of the effector T cell pool." J Exp Med 198(9): 1369-80.

Hendriks, J., Y. Xiao, et al. (2005). "During viral infection of the respiratory tract, CD27, 4-1BB, and OX40 collectively determine formation of CD8+ memory T cells and their capacity for secondary expansion." J Immunol 175(3): 1665-76.

Huang, J., K. W. Kerstann, et al. (2006). "Modulation by IL-2 of CD70 and CD27 Expression on CD8+ T Cells: Importance for the Therapeutic Effectiveness of Cell Transfer Immunotherapy." J Immunol 176(12): 7726-35.

Kaech, S. M., J. T. Tan, et al. (2003). "Selective expression of the interleukin 7 receptor identifies effector CD8 T cells that give rise to long-lived memory cells." Nat Immunol 4(12): 1191-8.

Krop, I., A. de Fougerolles, et al. (1996). "Self-renewal of B-1 lymphocytes is dependent on CD19." Eur J. Immunol. 26(1): 238-242.

Lens, S. M., R. de Jong, et al. (1996). "Phenotype and function of human B cells expressing CD70 (CD27 ligand)." Eur J Immunol 26(12): 2964-71.

Lenschow, D. J., T. L. Walunas, et al. (1996). "CD28/B7 SYSTEM OF T CELL COSTIMULATION." Annual Review of Immunology 14(1): 233-258.

Murray, H. W., C. M. Lu, et al. (2003). "Modulation of T-Cell Costimulation as Immunotherapy or Immunochemotherapy in Experimental Visceral Leishmaniasis." Infect. Immun. 71(11): 6453-6462.

Napolitani, G., A. Rinaldi, et al. (2005). "Selected Toll-like receptor agonist combinations synergistically trigger a T helper type 1-polarizing program in dendritic cells." Nat Immunol 6(8): 769-76.

Quezada, S. A., L. Z. Jarvinen, et al. (2004). "CD40/CD154 interactions at the interface of tolerance and immunity." Annu Rev Immunol 22: 307-28.

Ridge, J. P., F. Di Rosa, et al. (1998). "A conditioned dendritic cell can be a temporal bridge between a CD4+ T-helper and a T-killer cell." Nature 393(6684): 474-478.

Rowley, T. F. and A. Al-Shamkhani (2004). "Stimulation by Soluble CD70 Promotes Strong Primary and Secondary CD8+ Cytotoxic T Cell Responses In Vivo." J Immunol 172(10): 6039-6046.

Slavin, s. and s. Strober (1978). "Spontaneus murine B-cell leukaemia." nature 272(5654): 624-626.

Taraban, V. Y., T. F. Rowley, et al. (2004). "Cutting Edge: A Critical Role for CD70 in CD8 T Cell Priming by CD40-Licensed APCs." J Immunol 173(11): 6542-6546.

Tesselaar, K., Y. Xiao, et al. (2003). "Expression of the Murine CD27 Ligand CD70 In Vitro and In Vivo." J Immunol 170(1): 33-40.

Toes, R. E. M., S. P. Schoenberger, et al. (1998). "CD40-CD40Ligand interactions and their role in cytotoxic T lymphocyte priming and anti-tumor immunity." Seminars in Immunology 10(6): 443-448.

Tutt, A. L., L. O'Brien, et al. (2002). "T Cell Immunity to Lymphoma Following Treatment with Anti-CD40 Monoclonal Antibody." J Immunol 168(6): 2720-2728.

van Mierlo, G. J. D., A. T. den Boer, et al. (2002). "CD40 stimulation leads to effective therapy of CD40-tumors through induction of strong systemic cytotoxic T lymphocyte immunity." PNAS 99(8): 5561-5566.

Vonderheide, R. H., J. P. Dutcher, et al. (2001). "Phase I study of recombinant human CD40 ligand in cancer patients." J Clin Oncol 19(13): 3280-7.

Watts, T. H. (2005). "TNF/TNFR family members in costimulation of T cell responses." Annu Rev Immunol 23: 23-68.

The invention claimed is:

1. An in vivo method of treating cancer comprising administering a therapeutically effective amount of an agonistic anti-human CD27 antibody, or an agonistic antigen binding fragment thereof, wherein (i) said anti-human CD27 agonistic antibody or agonistic anti-human CD27 antibody fragment elicits an antitumor immune response in vivo by promoting the proliferation of tumor-associated antigen-specific T cells, and ii) said agonistic anti-human CD27 antibody or agonistic anti-human CD27 antibody fragment is capable of eliciting anti-tumor immunity when administered in the absence of another anti-cancer agent.

2. The method of claim 1, wherein said agonistic anti-human CD27 antibody or agonistic anti-human CD27 antibody fragment promotes the proliferation and/or survival of at least one of naïve or non-naïve CD8+ T cells, CD8+ effector cells, or CD8+ memory T cells.

3. The method of claim 1, wherein said agonistic anti-human CD27 antibody or agonistic anti-human antibody fragment is selected from a human antibody, a chimeric antibody containing a human constant region, a humanized antibody, a bispecific antibody, a primatized antibody, or a single chain antibody.

4. The method of claim 1, wherein said agonistic anti-human CD27 antibody or agonistic anti-human CD27 antibody fragment comprises at least one human constant domain selected from IgG1, IgG2, IgG3, IgG4, IgM, IgA1, IgA2, IgD, or IgE constant domains.

5. The method of claim 1, wherein said agonistic anti-human CD27 antibody or agonistic anti-human CD27 antibody fragment comprises an intact IgG1 antibody, an intact IgG2 antibody, an intact IgG3 antibody, an intact IgG4 antibody, and intact IgM antibody, an intact IgA1 antibody, an intact IgA2 antibody, an intact secretory IgA antibody, an intact IgD antibody, or an intact IgE antibody.

6. The method of claim 1, wherein said agonistic anti-human CD27 antibody or agonistic anti-human CD27 antibody fragment is glycosylated.

7. The method of claim 1, wherein said agonistic anti-human CD27 antibody or agonistic anti-human CD27 antibody fragment possesses at least one of the following properties:
   (a) recognizes an extracellular portion of human CD27;
   (b) the binding thereof to CD27 is not affected by human CD70;
   (c) it competes with CD70;
   (d) it is engineered to modify (enhance or diminish) binding to antibody effector systems;
   (e) it is modified to alter at least one of Fc glycosylation, binding to FcR, binding to FcRn, and interaction with complement system's proteins;
   (f) it comprises one or more modifications that are selected from modifications that reduce or enhance interaction with proteins of the complement system, or reduce undesirable toxicity including the undesirable release of cytokines.

8. The method of claim 1, wherein said agonistic anti-human CD27 antibody or agonistic anti-human CD27 antibody fragment is administered as a monotherapy.

9. The method of claim 1, wherein said method further comprises administering an antitumor vaccine containing a tumor-associated antigen.

10. The method of claim 9, wherein said vaccine is an antitumor vaccine and the agonistic anti-human CD27 antibody or agonistic anti-human CD27 antibody fragment is administered before, after or in conjunction with the vaccine.

11. The method of claim 9, wherein the tumor-associated antigen is a melanoma antigen and the combination enhances the immune response elicited against the tumor cells which express the target antigen.

12. The method of claim 1, wherein said cancer expresses CD40.

13. The method of claim 1, wherein said cancer is selected from leukemia, acute lymphocytic leukemia, acute myelocytic leukemia, myeloblastic promyelocytic myelomonocytic monocytic erythroleukemia, chronic leukemia, chronic myelocytic (granulocytic) leukemia, chronic lymphocytic leukemia, Polycythemia vera Lymphoma, Hodgkin's disease, non-Hodgkin's disease, multiple myeloma, Waldenstrom's macroglobulinemia, heavy chain disease, solid tumors, sarcomas, carcinomas, fibrosarcoma, myxosarcoma, liposarcoma, chrondrosarcoma, osteogenic sarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon sarcoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, retinoblastoma, nasopharyngeal carcinoma, and esophageal carcinoma.

14. The method of claim 1, wherein said cancer is selected from breast, liver, ovarian, renal, colorectal, lung, stomach, kidney, melanoma, leukemia or lymphoma.

15. The method of claim 1, wherein said cancer comprises a solid tumor.

16. The method of claim 14, wherein said lymphoma or leukemia is non-Hodgkin's lymphoma or chronic lymphocytic leukemia.

17. The method of claim 1, wherein said agonistic anti-human CD27 antibody or agonistic anti-human CD27 antibody fragment binds FcR.

18. The method of claim 1, wherein said agonistic anti-human CD27 antibody or agonistic anti-human CD27 antibody fragment comprises a human IgG1 or IgG3 constant region.

* * * * *